(12) United States Patent
Keimel et al.

(10) Patent No.: US 8,419,710 B2
(45) Date of Patent: Apr. 16, 2013

(54) METHODS FOR INFUSING FLUIDS VIA AN IMPLANTABLE INFUSION SYSTEM

(75) Inventors: John G. Keimel, North Oaks, MN (US); William F. Kaemmerer, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 1161 days.

(21) Appl. No.: 11/951,755

(22) Filed: Dec. 6, 2007

(65) Prior Publication Data

US 2008/0140048 A1 Jun. 12, 2008

Related U.S. Application Data

(60) Provisional application No. 60/868,901, filed on Dec. 6, 2006, provisional application No. 60/868,904, filed on Dec. 6, 2006.

(51) Int. Cl.
*A61M 31/00* (2006.01)
*A61M 1/00* (2006.01)

(52) U.S. Cl.
USPC .......................................... 604/508; 604/151

(58) Field of Classification Search .................. 604/131, 604/151, 264, 265, 280, 282, 283, 284, 508
See application file for complete search history.

(56) References Cited

U.S. PATENT DOCUMENTS

| | | | | |
|---|---|---|---|---|
| 4,866,042 A * | 9/1989 | Neuwelt | ....................... | 424/93.2 |
| 5,433,946 A * | 7/1995 | Allen et al. | ................... | 424/94.3 |
| 5,702,372 A * | 12/1997 | Nelson | .......................... | 604/264 |
| 5,798,366 A * | 8/1998 | Platt et al. | ...................... | 514/315 |
| 6,048,729 A * | 4/2000 | Selden et al. | ................. | 435/455 |
| 6,302,685 B1 * | 10/2001 | Lobel et al. | ....................... | 433/6 |
| 6,410,250 B1 * | 6/2002 | Gueiros-Filho et al. | ...... | 435/7.22 |
| 6,663,609 B2 * | 12/2003 | Williamson et al. | ...... | 604/288.01 |
| 2001/0031741 A1 * | 10/2001 | Ziegler et al. | ................... | 514/44 |
| 2002/0119923 A1 * | 8/2002 | Benowitz | ........................ | 514/12 |
| 2003/0078562 A1 * | 4/2003 | Makower et al. | ............ | 604/509 |
| 2003/0181426 A1 * | 9/2003 | Eisenach | ....................... | 514/161 |
| 2005/0042227 A1 * | 2/2005 | Zankel et al. | .............. | 424/178.1 |
| 2005/0048641 A1 * | 3/2005 | Hildebrand et al. | ........ | 435/283.1 |
| 2005/0208090 A1 * | 9/2005 | Keimel et al. | ................. | 424/423 |
| 2006/0282043 A1 * | 12/2006 | Pyles | ....................... | 604/170.03 |
| 2008/0140056 A1 * | 6/2008 | Keimel et al. | .............. | 604/891.1 |

* cited by examiner

*Primary Examiner* — Kevin C Sirmons
*Assistant Examiner* — William Carpenter

(57) ABSTRACT

Methods for delivering first and second fluid compositions to a target location of a subject include delivering the first composition from reservoir of an implantable infusion pump and delivering the second composition through a catheter access port of the implantable infusion device. The access port and reservoir are fluidly coupled to a catheter having a delivery region implanted in the target region. The methods more fully realize the therapeutic potential of infusion devices having both an access port and a reservoir. Strategic use of different agents that compliment the function of each other delivered via either the access port or the reservoir can result in enhanced therapeutic potential.

4 Claims, 15 Drawing Sheets

METHODS FOR INFUSING FLUIDS VIA AN IMPLANTABLE INFUSION SYSTEM

RELATED APPLICATIONS

This Application claims the benefit of Provisional Application Ser. No. 60/868,901, filed Dec. 6, 2006, and of Provisional Application Ser. No. 60/868,904, filed Dec. 6, 2006, which applications are hereby incorporated herein by reference in their respective entireties to the extent that they do not conflict with the present disclosure.

FIELD

The present disclosure relates to medical devices and systems and methods associated therewith; more particularly, to infusion devices and systems and methods associated therewith.

BACKGROUND

Implantable infusion devices have been employed to treat a variety of diseases such as pain, spasticity, and cancer. For some medical conditions, medical devices provide the best, and sometimes the only, therapy to restore an individual to a more healthful condition and a fuller life.

Many infusion devices have a reservoir that houses a therapeutic composition. The therapeutic composition may be delivered via an infusion region of a catheter fluidly coupled to the reservoir. The therapeutic composition placed in the reservoir, and the target implant location of the delivery region, can be selected based on the disease to be treated. Often, the infusion devices are configured, so the reservoir can be replenished with the therapeutic composition through a septum of a refill port while the pump is implanted. This is commonly done by injecting a hypodermic needle through the skin and into the septum thereby providing access to refill the reservoir.

In such devices a catheter access port is often provided in addition to the refill port. The catheter access port is also accessible percutaneously by hypodermic needle. Its septum provides direct access to the catheter bypassing the reservoir and allows a bolus of a therapeutic composition to be administered directly into the body at the site of the catheter. The catheter access port can also be used as a diagnostic tool to troubleshoot the catheter or infusion problems.

While implantable infusion devices that have refillable reservoirs and catheter access ports are known, the therapeutic advantages of the use of the reservoirs in combination with the access ports to provide improved therapy has not been fully explored.

SUMMARY

The present disclosure describes methods for providing therapy that combines the therapeutic potential of chronic delivery of a therapeutic agent from a reservoir of an implantable infusion device with the more acute delivery potential of an access port of the device.

In an embodiment, a method for infusing first and second fluid compositions to a target location of a subject using an implantable infusion system including an infusion device and a catheter is described. The infusion device has a reservoir and a catheter access port, and the catheter has a delivery region and is operably couplable to the infusion device such that fluid stored in the reservoir or infused into the access port is deliverable via the delivery region to a target location of the subject. The method includes introducing into the reservoir the first fluid composition including a first polypeptide configured to function as an endogenous protein, and delivering the first fluid composition to the target location via the delivery region of the catheter. The method also includes delivering to the target location the second fluid composition that contains a polynucleic acid encoding a second polypeptide configured to function as the endogenous protein. The second fluid composition is infused into the catheter access port. The first and second polypeptides can be the same or different.

In another embodiment, a method includes dispensing into the reservoir the first fluid composition comprising an inhibitory polynucleic acid agent configured to suppress expression of a target protein, and delivering the first fluid composition to the target location via the delivery region of the catheter. The method also includes delivering to the target location the second fluid composition that contains a replacement polypeptide therapy for the suppressed target protein. The second fluid composition is infused into the catheter access port.

The well developed therapeutic strategies presented herein allow for advantageous therapeutic use of infusion devices having a reservoir and a catheter access port. One advantage in various embodiments is the ability to deliver two different agents to the same location to provide for increased therapeutic potential, particularly when the two agents are selected to compliment each other as described herein. These and other advantages will be readily understood by one of skill in the art upon reading the disclosure presented herein.

Figure 1:
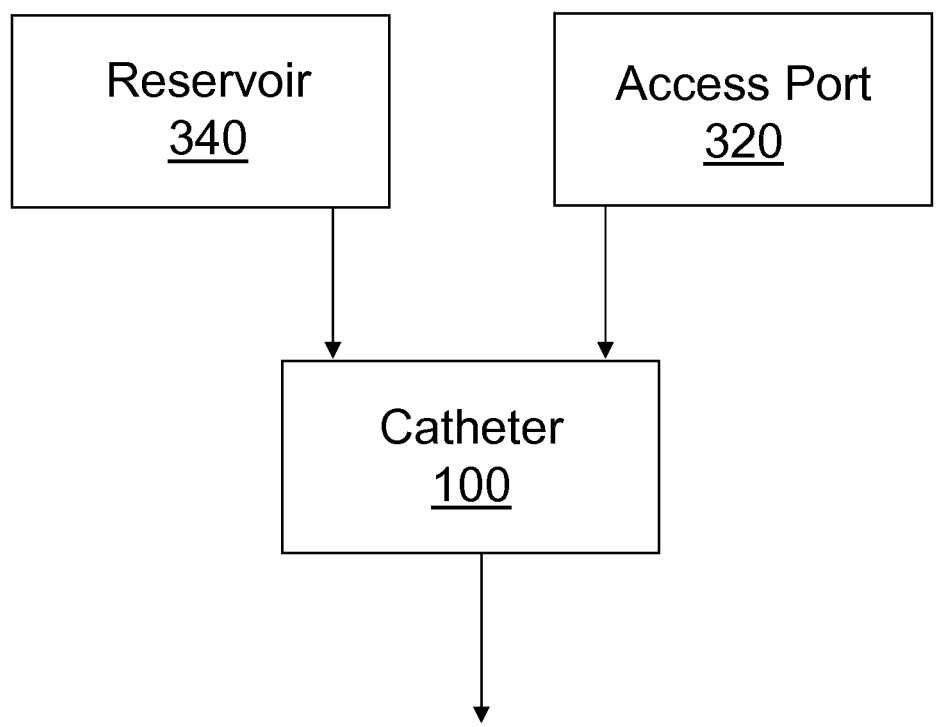
FIG. 1 is a schematic block diagram of components of representative infusion system.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

I. Definitions

All scientific and technical terms used herein have meanings commonly used in the art unless otherwise specified. The definitions provided herein are to facilitate understanding of certain terms used frequently herein and are not meant to limit the scope of the present disclosure.

As used herein, "subject" means an animal into which a catheter or a portion thereof may be implanted and includes mammals, such as humans.

As used herein, "treat" means to subjectively or objectively alleviate at least one symptom of a disease.

As used herein, "disease" means a condition of a subject or a portion thereof that impairs normal functioning and is typically manifested by signs or symptoms. Condition, disease, disorder and the like are used herein interchangeably. Sign and symptom are used herein interchangeably.

As used herein, "large molecule" means a molecule having a peptide bond, such as a polypeptide, or a molecule having a phosphodiester bond, such as a polynucleic acid.

As used herein, "polypeptide" means a molecule comprising an amino acid or a derivative thereof joined by a peptide bond to another amino acid or derivative thereof and typically refers to a protein having an activity on a biological system. It will be understood that referral to a specific polypeptide, such as leptin, includes any polypeptide having activity substantially similar to the specific polypeptide.

As used herein, "nucleic acid" means a molecule comprising a nucleotide or nucleoside or derivative thereof. A "polynucleic acid", as used herein, means molecule comprising a nucleotide, nucleoside, or a derivative thereof joined to another nucleotide, nucleoside, or a derivative thereof via a phosphodiester bond. It will be understood that referral to a polynucleic acid encoding a specific polypeptide includes a nucleic acid encoding any polypeptide having activity substantially similar to the specific polypeptide.

As used herein, "comprising", "including", and the like are used in an open-ended fashion, and thus should be interpreted to mean "including, but not limited to . . . ".

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

II. Infusion System

Any implantable infusion device having a reservoir and an access port fluidly coupled to an infusion catheter may be employed to carry out a method as described herein.

Referring to FIG. 1, a block diagram of a representative infusion system is shown. A reservoir 340 of an implantable infusion device is fluidly coupled to a catheter 100 which can deliver fluid from the reservoir 340 to a target location of a subject. As shown in FIG. 1, an access port 320 is also fluidly coupled to the catheter 100 such that fluid infused into access port 320 is directed through catheter 100 to the target location of the subject. A filter (not shown) may be placed between reservoir 340 and catheter 100 or access port 320 and catheter 100 to prevent introduction of bacterial contaminants into the catheter.

Figure 2:
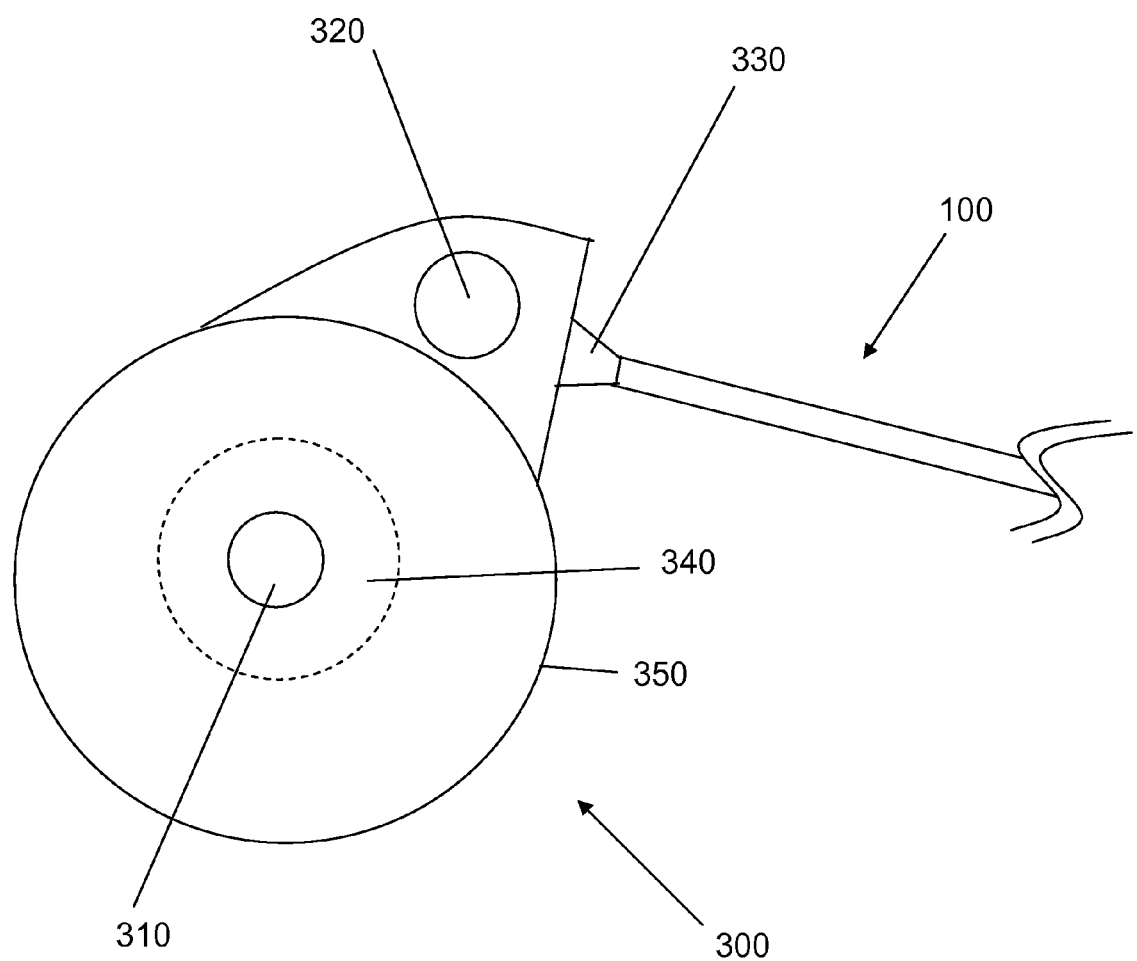
FIG. 2 is a schematic diagram of a side view of an infusion device and catheter.

Referring to FIG. 2, a representative implantable infusion system is shown. A catheter 100 is connected to an infusion device 300 via a catheter connector 330. Infusion device 300 shown in FIG. 2 includes a refill port 310 in fluid communication with a reservoir 340 (shown with dashed lines to indicate that reservoir 340 is beneath hermetically sealed housing 350) for containing a fluid to be infused to into a subject via catheter 100, which is in fluid communication with reservoir 340. The depicted infusion device 300 also includes a catheter access port 320, which is in fluid communication with catheter 100. Fluid, e.g. fluid containing therapeutic agent, may be injected into catheter access port 320, e.g. to deliver a bolus of therapeutic agent. Examples of infusion devices 300 having injection ports 310 in fluid communication with reservoirs and having catheter access ports 320 are Medtronic, Inc.'s SynchroMed® series of infusion devices. Infusion device 300 may include an active or passive mechanism for delivering fluid through catheter 100. For example, reservoir 340 may be operably coupled to a pump (not shown) disposed with housing 350, such as an osmotic, peristaltic, or piston pump, or the like. Of course, reservoir 340 and access port 320 may be housed in separate devices.

Figure 3:
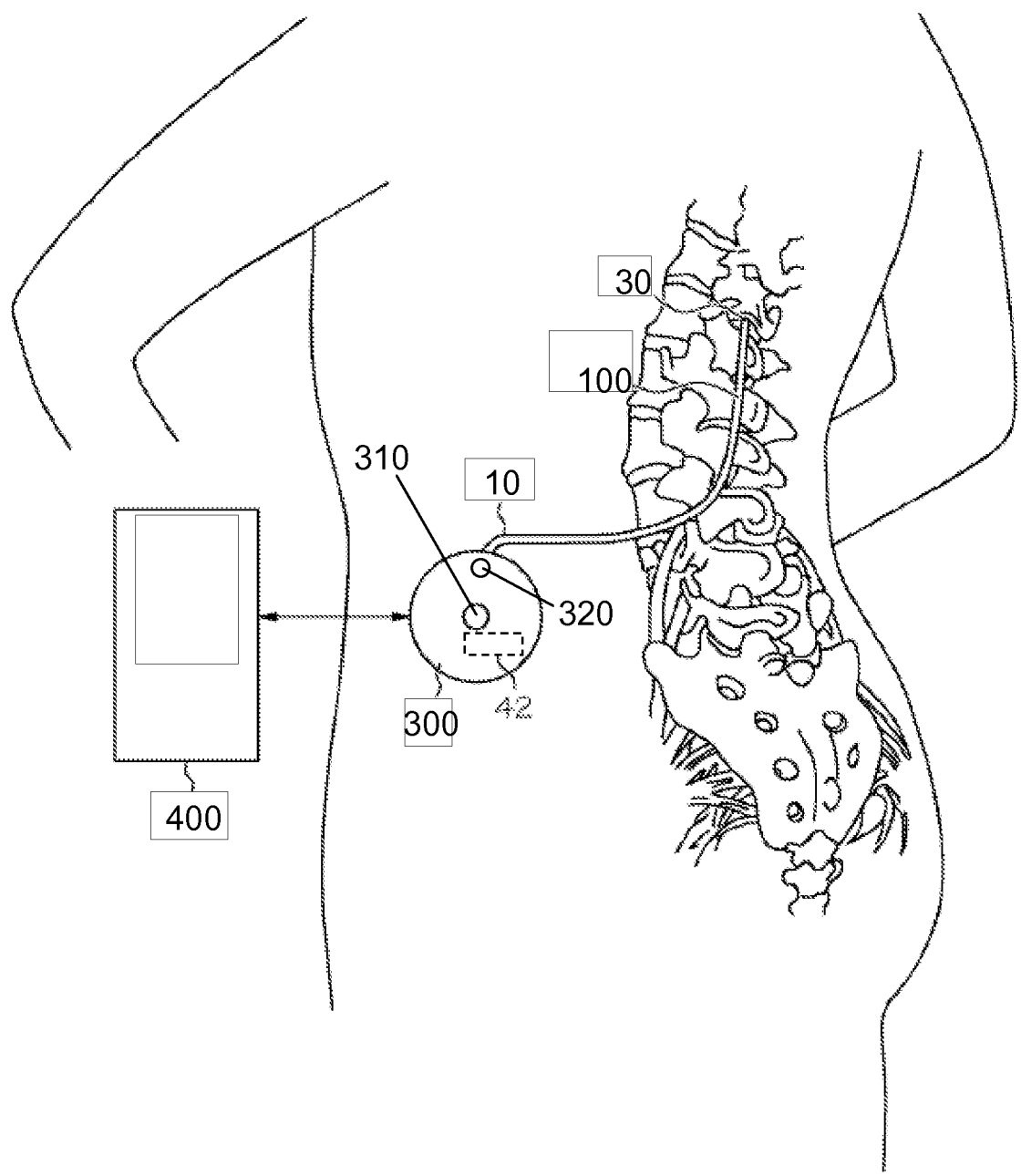
FIG. 3 is a schematic diagram showing a representative infusion system implanted in a subject.

Referring to FIG. 3, a programmable infusion device 300, such as Medtronic, Inc.'s SynchroMed® series of infusion devices, is shown implanted in a human. As shown in FIG. 3, distal end 30 of catheter 100 may be inserted into a subject's spinal canal through a lumbar puncture and advanced rostrally through the spinal canal to a desired location. Of course, therapeutic fluid may be directed to any desired location in a subject by proper placement of the catheter, such as the portal vein or hepatic artery, a carotid artery, or the tissue of an organ, such as the brain. Proximal end 10 of catheter 100 is coupled to infusion device 300, which is typically implanted in the subject at a subcutaneous location. Infusion device 300 comprises a receiver 42 (or transmitter) which is capable of telemetric communication (or any other suitable form of communication) with programmer 400. Programmer 400 may communicate with implantable infusion device 300 to adjust the amount of therapeutic agent delivered. Communication may be unidirectional; e.g., programmer 400 to infusion device 300, or bi-directional. While not shown, it will be understood that one or more sensors may be operably coupled to infusion device 300 to alter the rate at which therapeutic agent is delivered. Programmable infusion devices are particularly amenable to alteration of infusion rate via sensors.

One advantage of the use of programmable infusion devices over non-programmable devices is that the rate of delivery of therapeutic agent from infusion device 300 may be altered as a subject's condition warrants or to optimize therapeutic efficacy. As described herein, it may be desirable to administer a substantially constant low level of therapeutic agent to keep catheter 100 patent while implanted and to deliver intermittent bolus dosages of therapeutic agent to achieve broad distribution of therapeutic agent and enhance efficacy. Such a delivery profile is readily obtainable through the use of programmable infusion devices.

Figure 4:
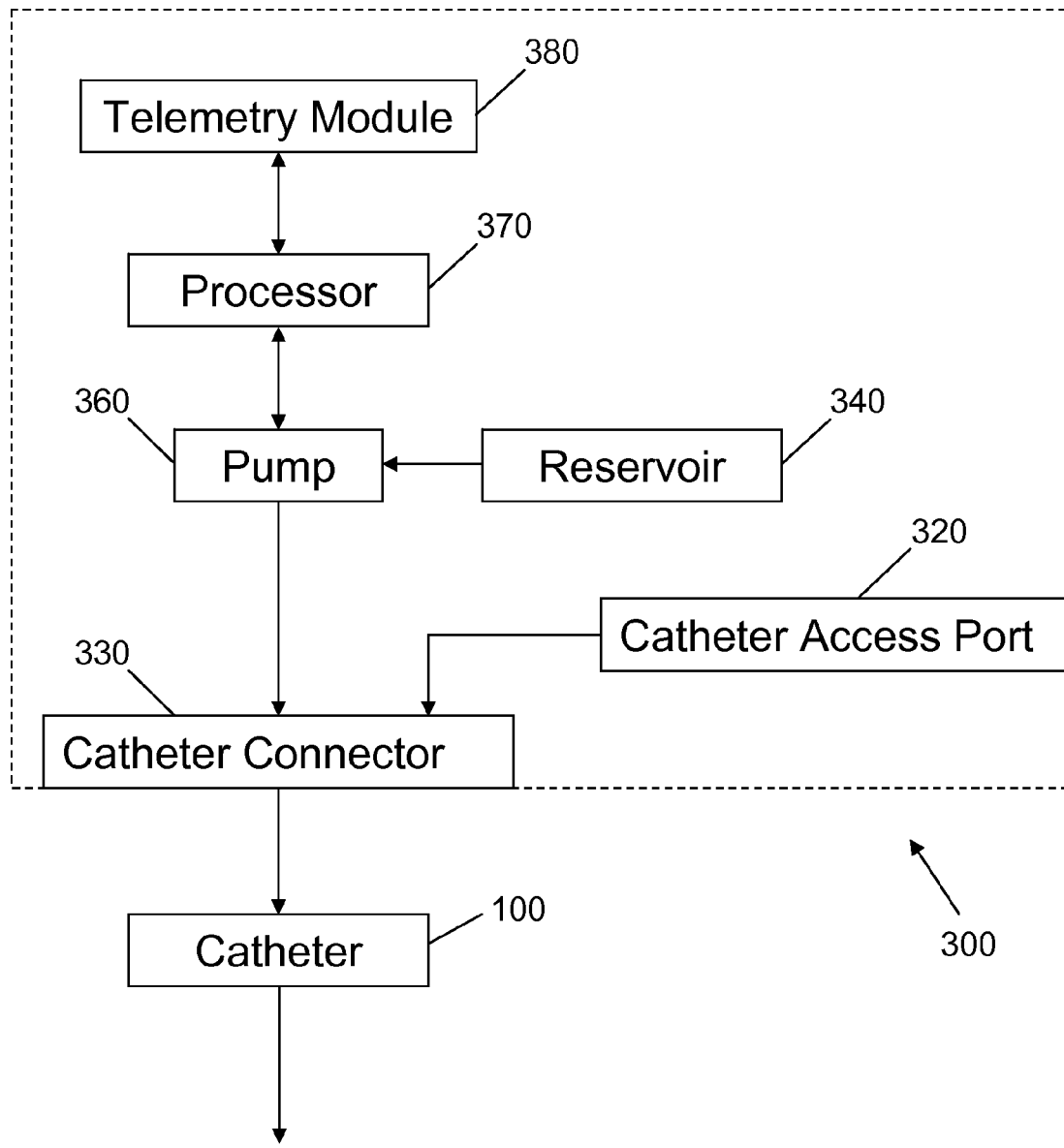
FIG. 4 is a schematic block diagram of components of representative infusion system.

Referring now to FIG. 4, a block diagram of selected components of a representative infusion system is shown. The system includes an implantable infusion device 300 and a catheter 100 operably coupled to the infusion device 300 via a catheter connector 330. The infusion device 300 includes a pump 360 operably coupled to a reservoir 340 to deliver fluid to catheter 100. A processor 370 is operable coupled to the pump 360 to control the amount of fluid delivered from reservoir 340 to catheter 100. As depicted, the infusion device 300 may further include a telemetry module 380 for communication with a remote device, such as an external programmer 400 (see FIG. 3). The infusion device 300 also includes a catheter access port 310 fluidly coupled to catheter 100 via catheter connector 330. It will be understood that infusion devices suitable for use with the methods described herein may include additional components or may omit some of the components illustrated in FIG. 4.

In general, it will be understood that catheter 100, or portions thereof, may be made of any material that is compatible with a subject in which catheter 100 is implanted and with fluid to be delivered through catheter 100. Material selection for the catheter may be based on mechanical properties of the tubing, drug stability (changes in the drug due to the catheter material), drug compatibility (changes in the catheter material due to the drug), biostability (changes in the material due to the in vivo environment), biocompatibility (effects of the material on the subject), and the like. Generally catheter 100 or portions thereof will be made of polymeric material such as silicone, polyurethane, polyethylene, polypropylene, and the like. If polypeptides are to be delivered via catheter 100, it may be desirable to use polymeric materials other than silicone, as the polypeptide may adhere to or be absorbed into the silicone or may be degraded, or to coat lumen 40 of a silicon catheter 100 with a material, such as a suitable polymeric material, to reduce adherence or absorbance of the polypeptide.

Figure 5:
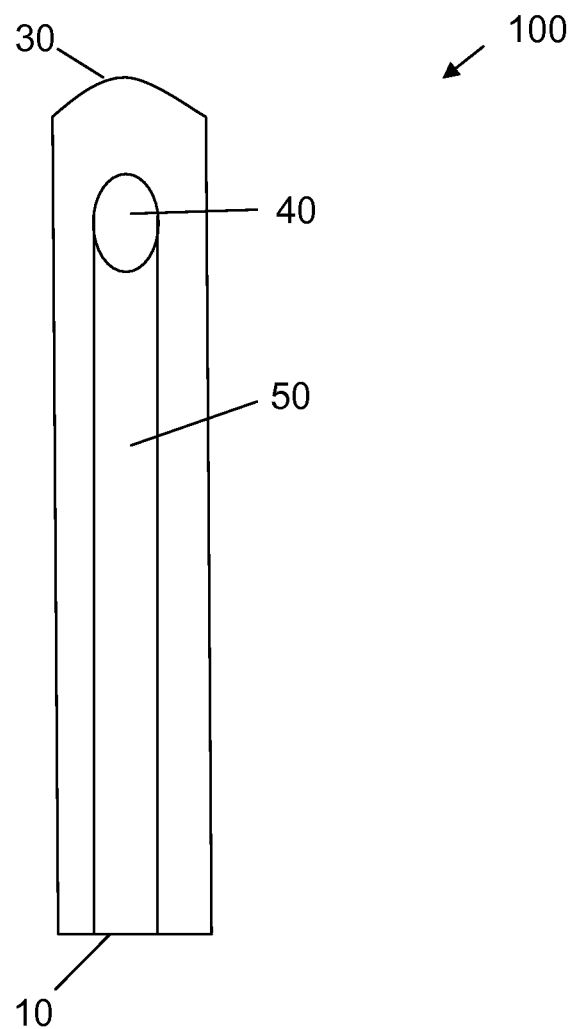
FIG. 5 is a schematic diagram of a longitudinal section of a representative catheter.

Referring now to FIG. 5, a longitudinal cross section of a representative catheter 100 is shown. Catheter 100 has a proximal end 10 and a distal end 30. Proximal end 10 is configured to be coupled to an infusion device 300 (see, e.g., FIG. 1). Proximal end 10 of catheter 100 may be coupled to infusion device 300 using any known or future developed mechanism. Of course, catheter 100 may be coupled to another piece of tubing (not shown) via a connector (not shown) and the other piece of tubing can be coupled to infusion device 300, provided that lumen 50 of catheter 100 is in fluid communication with a reservoir and an access port.

As shown in FIG. 5, a delivery region 40 is located between proximal end 10 and distal end 30. Catheter 100 comprises a lumen 50 extending from proximal end 10 to delivery region 40. Delivery region 40 in FIG. 5 is depicted as a side hole. However, it will be recognized that delivery region 40 may be one or more side holes, one or more porous regions (not shown) that extend around or substantially around a portion catheter 100, an opening (not shown) at distal end 30, or the like. It may be desirable in many circumstances to have more than one opening for fluid to be delivered or withdrawn in case one or more openings becomes clogged during or following implantation of catheter 100.

In various embodiments, catheter 100 is configured to deliver fluid to the cisterna magna (see FIG. 13) of a subject. In such embodiments, catheter 100 may be as described in copending U.S. patent application Ser. No. 11/951,771, entitled "Intrathecal Catheter", having, and filed on the same date herewith, which copending application is hereby incorporated herein by reference in its entirety to the extent that it does not conflict with the disclosure presented herein.

III. Representative Methods

While the representative methods described below refer to use of catheter 100 and infusion device 300, as described above, it will be understood that any suitable catheter or infusion device may be employed in the described methods.

Various methods for delivering first and second fluid compositions to a target location of a subject using an implantable infusion system including an infusion device 300 and a catheter 100 are contemplated. One representative method is illustrated in the flow diagram depicted in FIG. 6. The method includes implanting an infusion device 300 having a reservoir 340 and a catheter access port 320 in a subject (2000). The depicted method also includes implanting a catheter 100 in the subject such that a delivery region 40 is positioned at a target location of the subject (2010). The method further includes fluidly coupling the catheter 100 to the reservoir 340 and the access port 320 (2020). As used herein in, "fluidly couple" means to operably couple two or more devices or components such that the devices or components are in fluid communication. This can be accomplished, e.g., by connecting proximal end 10 of catheter 100 to a catheter connector 330 of the infusion device 300 to which reservoir 340 and access port 320 are fluidly coupled. The depicted method includes introducing or dispensing a first fluid composition into the reservoir 340 (2030), e.g. via a refill port 320. The method further includes delivering the first fluid composition to the target location from the reservoir 340 via the delivery region 40 of the catheter 100 (2040). The depicted method also includes delivering to the target location a second fluid composition by infusing the second fluid composition into the access port 320 (2050).

Figure 6:
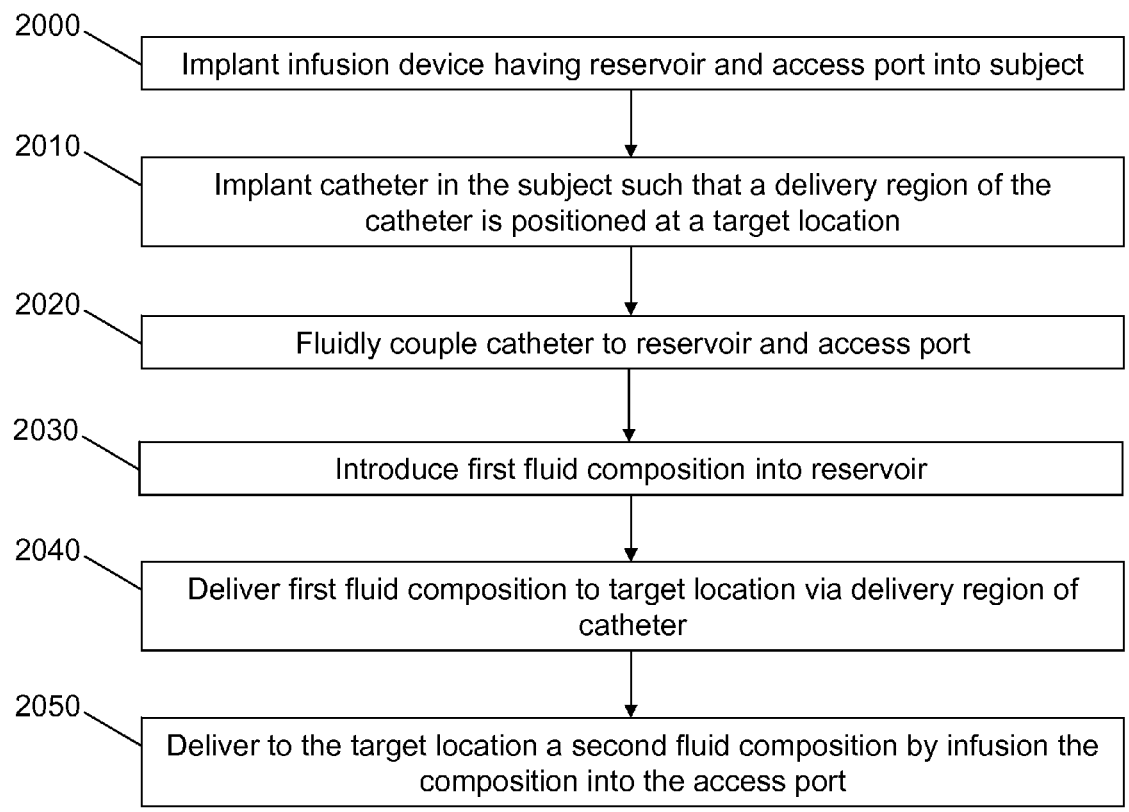
FIGS. 6-12 are flow diagrams illustrating representative methods.

The method illustrated in FIG. 6 may be employed in numerous fashions to combine the therapeutic potential of chronic delivery of a therapeutic agent from a reservoir 340 of an implantable infusion device 300 with the more acute delivery potential of an access port 320 of the device 300. Some representative examples of strategies intended to exploit this potential are described below.

The method illustrated in FIG. 6 may prove advantageous for protein replacement therapy in subjects lacking a protein, under-expressing a protein, or having a dysfunctional protein. As used herein, "dysfunction", in the context of a polypeptide, means that the dysfunctional polypeptide does not have the full activity of a non-dysfunctional (e.g., wild-type) polypeptide. For example a dysfunctional polypeptide receptor that is intended to be embedded in a cell membrane may be dysfunctional if (i) it is not properly located in the cell membrane, (ii) is not capable of binding agonist as well as non-dysfunctional receptor, (iii) does not properly couple to intracellular or intra-membrane molecules, (iv) etc. By way of further example, an enzyme is dysfunctional if it is not capable of catalyzing a reaction at a rate, amount, etc. of a wild-type enzyme.

For protein replacement therapy, the first fluid composition that is dispensed in the reservoir 340 may contain a replacement polypeptide. The second fluid composition that is infused into the access port 320 may contain a polynucleic acid encoding the protein or a functional variant or fragment thereof (referred to hereinafter as a "second polypeptide"). The second polypeptide may be the same or different than the replacement polypeptide. The delivery of the replacement polypeptide may be used to determine whether the subject would likely respond favorably to delivery of the polynucleic acid encoding the second polypeptide or to supplement the poynucleotide therapy if expression of the exogenous polynucleic acid wanes. It will be understood that because the catheter access port 320 is implanted in the subject and fluidly coupled to the catheter 100 periodic administration of the second fluid composition containing the polynucleic acid may be readily administered at periodic or other intervals as desired, e.g. if expression wanes.

Figure 7:
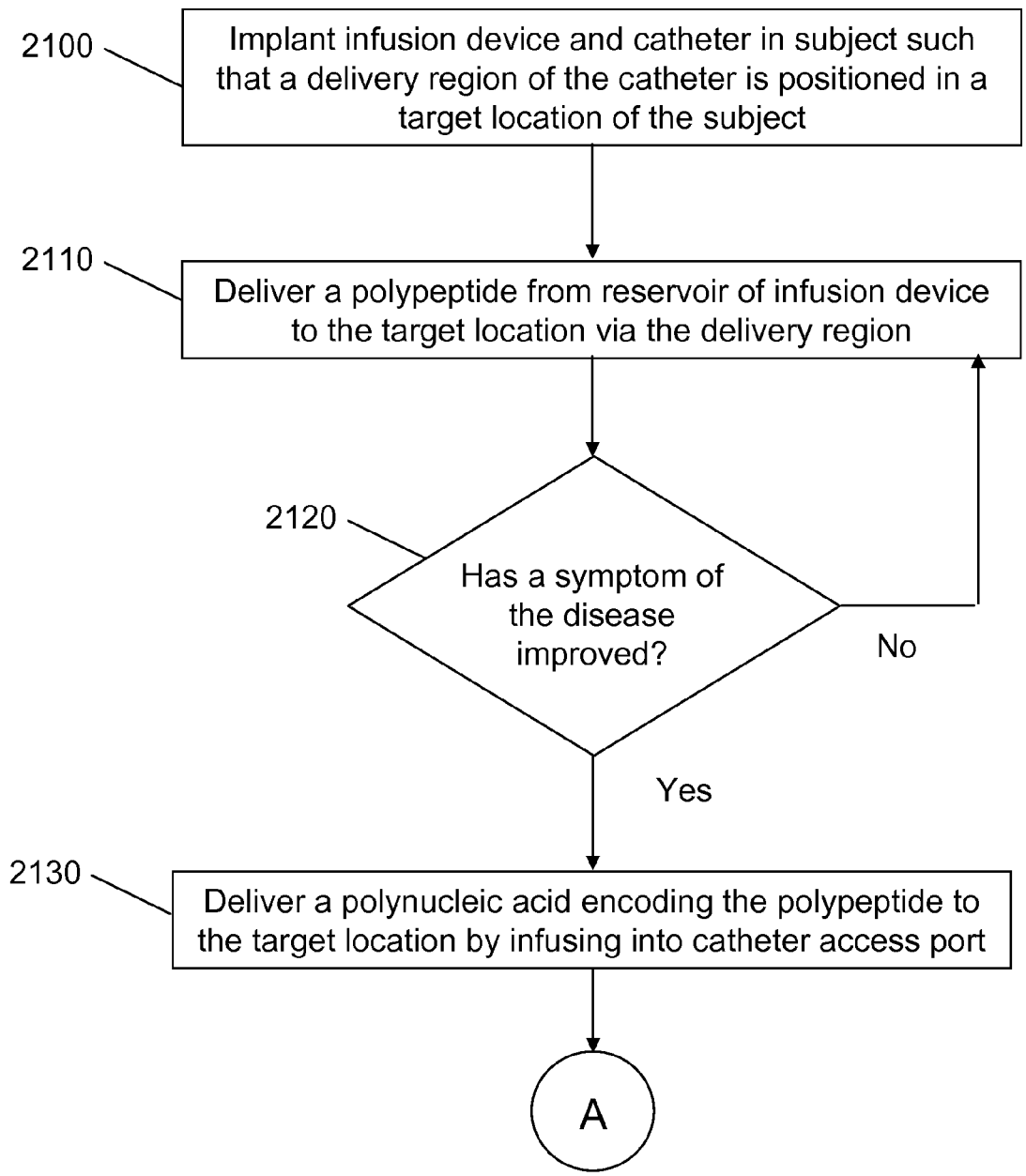

By way of example, and referring to FIG. 7, an infusion device 300 and a catheter 100 are implanted into a subject such that a delivery region 40 of the catheter 100 is positioned in a target location of the subject (2100), e.g. as described above with regard to FIG. 6. A replacement polypeptide may then be delivered from a reservoir 340 of the infusion device 300 to the target location via the delivery region 40 of the catheter 100 (2110). A determination may then be made as to whether a symptom of the disease for which protein replacement therapy is intended to treat has improved following delivery of the polypeptide (2120) and the introduction of the peptide into the subject has been well-tolerated by the subject. If no improvement is observed or detected or the therapy has not been well-tolerated by the subject, the dose of the polypeptide delivered may be adjusted, for example by providing telemetric instructions from a programmer device 400. Alternatively or following one or more dose adjustments, it may be decided that further therapy is not warranted. If an improvement has been observed or detected, a polynucleic acid encoding the second polypeptide may be delivered to the target location via the delivery region 40 of the catheter 100 (2130). The method depicted in FIG. 7 may be beneficial for determining whether a subject may be a suitable candidate for gene therapy. Because polypeptide therapy is easily reversible (e.g., by stopping delivery of the polypeptide), it may be desirable to determine whether a subject may respond favorably to polypeptide therapy before subjecting the subject to gene therapy, which may be more difficult to reverse or control.

Figure 8:
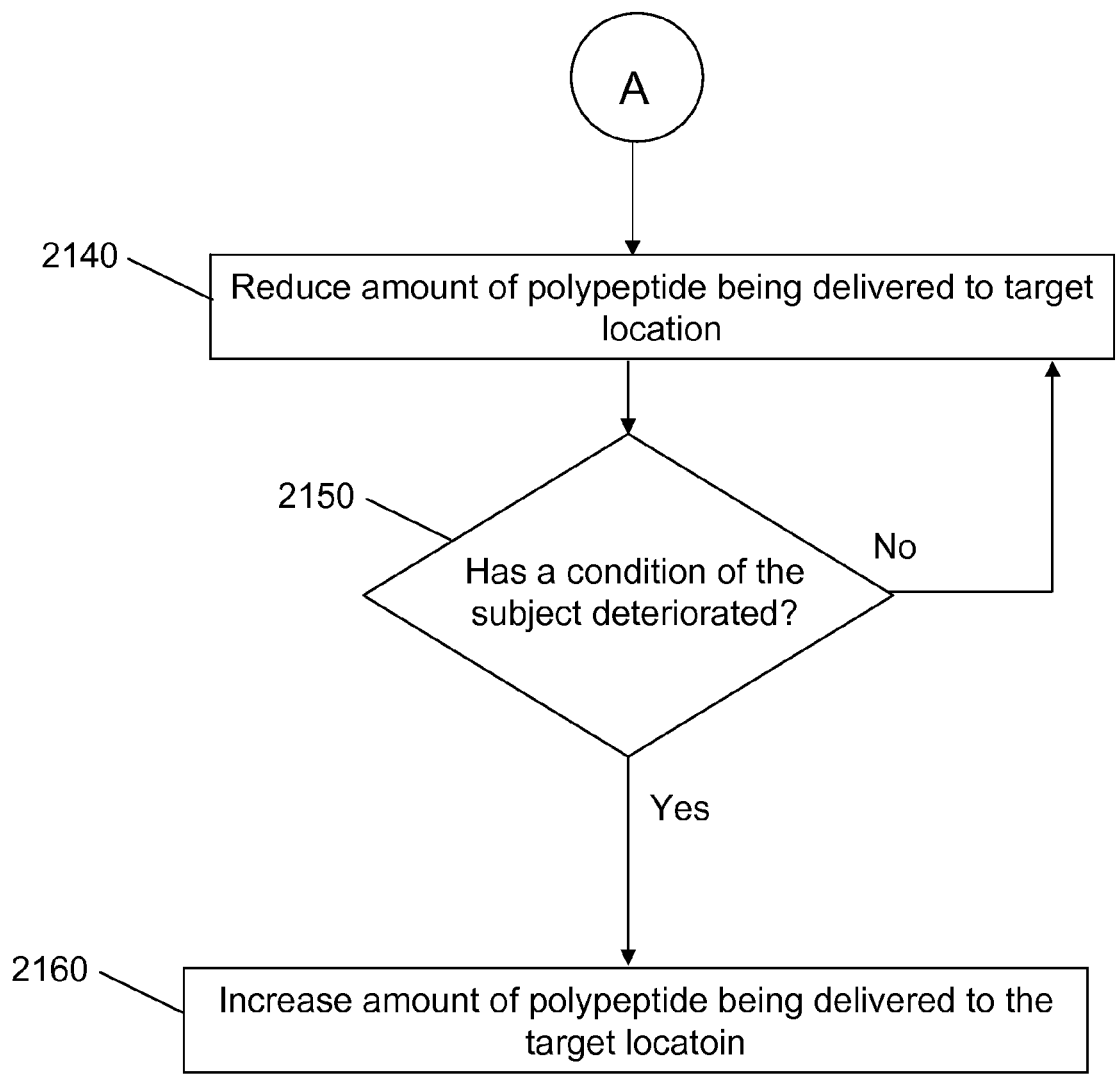

FIG. 8 depicts a process that may continue from the process depicted in FIG. 7. As shown in FIG. 8, the amount of replacement polypeptide delivered may be reduced (2140) following delivery of the polynucleic acid to the subject. A determination as to whether the condition of the subject has deteriorated may then be made (2150). If the condition of the subject has not deteriorated, the amount of the replacement polypeptide may be further reduced (2140), eventually until the replacement polypeptide is no longer being delivered. If the condition of the subject has deteriorated, the amount of replacement polypeptide being delivered may be increased (2150) to improve the subject's condition. By taking full advantage of an infusion device 300 having both a reservoir 340 and catheter access port 320 in fluid communication with a catheter 100 when implanted in a subject, delivery of a polypeptide and a polynucleic acid to the same target location may serve to enhance protein replacement therapy beyond that previously described.

Figure 9:
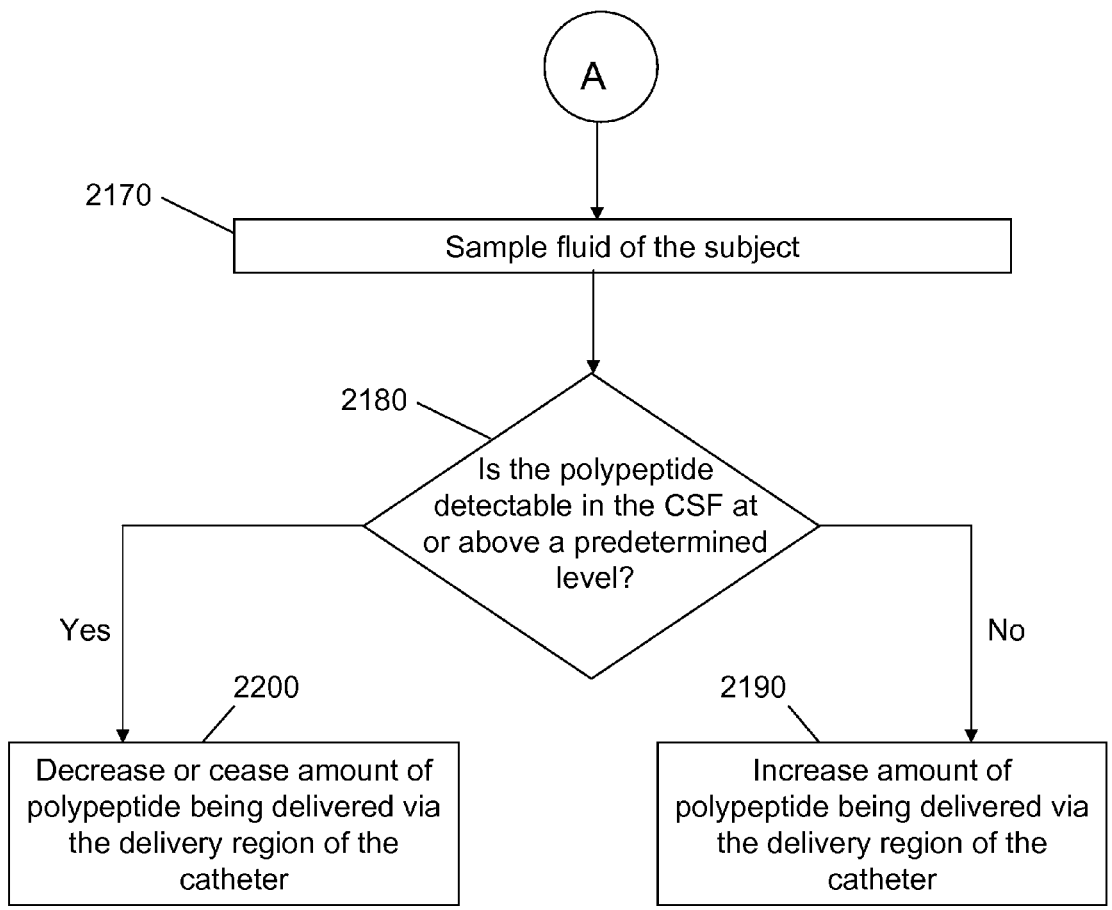

FIG. 9 shows another process that that may continue from the process depicted in FIG. 7. As shown in FIG. 9, extracellular fluid, blood, cerebrospinal fluid (CSF), or the like of the subject is sampled (2170), preferably after delivery of the polypeptide (2110) has ceased for a sufficient time to allow for clearance of the polypeptide from the subject. Most polypeptides delivered to subjects are no longer present within 48 hours following delivery. The fluid may be sampled through the same catheter 100 through the polypeptide and polynucleic acid is delivered, for example by withdrawing fluid via the catheter access port 320, or may be sampled via any other suitable technique. A determination is then made as to whether the second polypeptide is being adequately expressed from the polynucleic acid by determining whether the second polypeptide is detectable in the fluid (2180) at a suitable level. If the polypeptide is not detectable at high enough levels, the replacement polypeptide may be delivered (2190) to achieve suitable levels of the polypeptide. If the polypeptide is detectable at suitable levels, further delivery of the replacement polypeptide may be stopped (2200).

Figure 10:
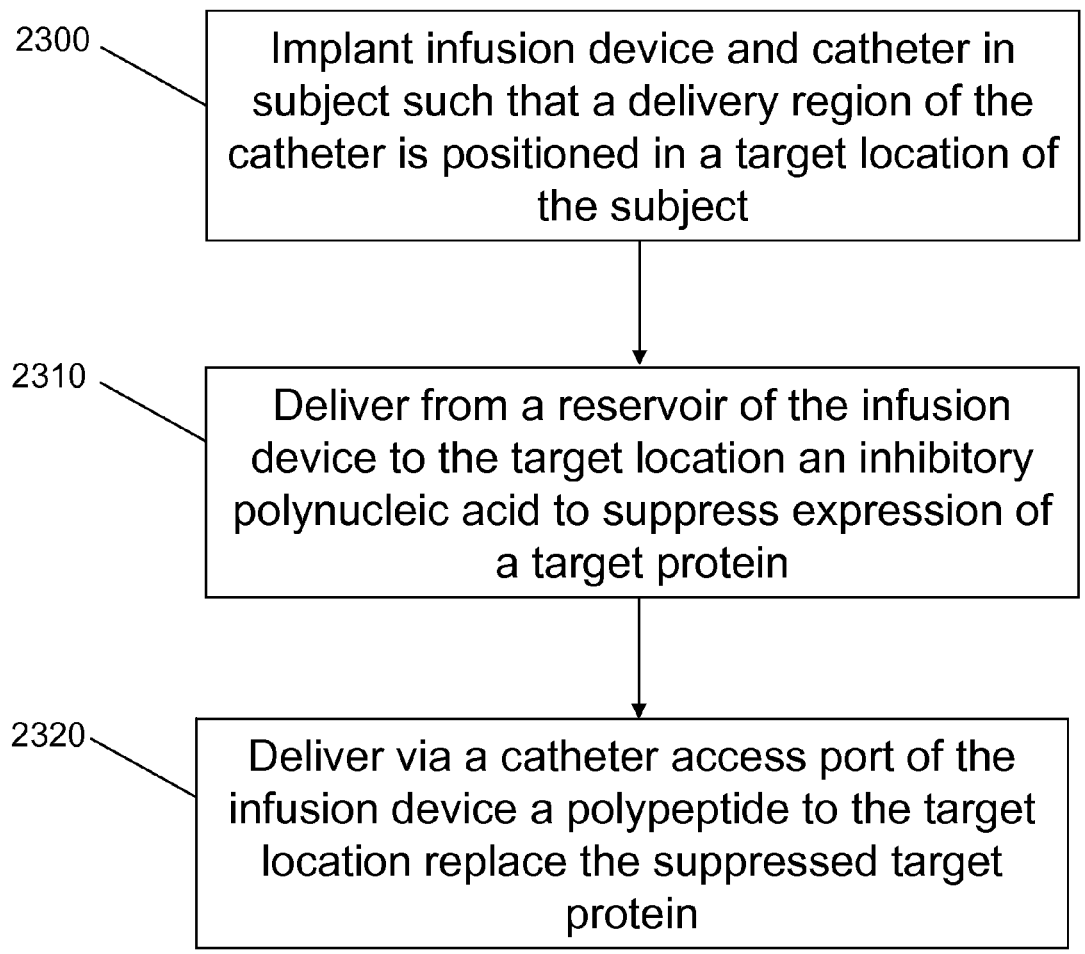

Referring now to FIG. 10, a flow diagram depicting another representative method is shown. Again, the method provides a basis for more fully realizing the potential of an implantable infusion device 300 having a reservoir 340 and a catheter access port 320. The method depicted in FIG. 10 is one where an inhibitory polynucleic acid is delivered in combination with a polynucleic acid encoding for a functional polypeptide. As used herein, "inhibitory polynucleic acid" means a polynucleic acid that reduces the expression of a target gene when delivered to a subject. Examples of inhibitory nucleic acids include siRNA, shRNA, ribozymes, and the like. Such a method allows for inhibition of the expression of a mutant polypeptide and replacement of the polypeptide to normal levels.

The method illustrated in FIG. 10 includes implanting the infusion device 300 and catheter 100 in a subject such that a delivery region 40 of the catheter 100 is positioned in a target location of the subject (2300), which may be done, for example, as described with regard to FIG. 6. An inhibitory polynucleic acid may then be delivered from a reservoir 340 of the infusion device 300 to the via the delivery region 40 of the catheter 100 to the target location (2310). The inhibitory polynucleic acid is configured to reduce or suppress expression of a target protein. A treatment intended to replace the function of the inhibited target protein may be delivered to the target location by infusing a fluid composition containing a polynucleic acid encoding for a replacement polypeptide into an access port 320 of the infusion device 300 (1220). Examples of a polynucleic acid encoding for a replacement polypeptide include non-viral vectors, viral vectors such as adeno-associated viral vectors, and the like.

Figure 11:
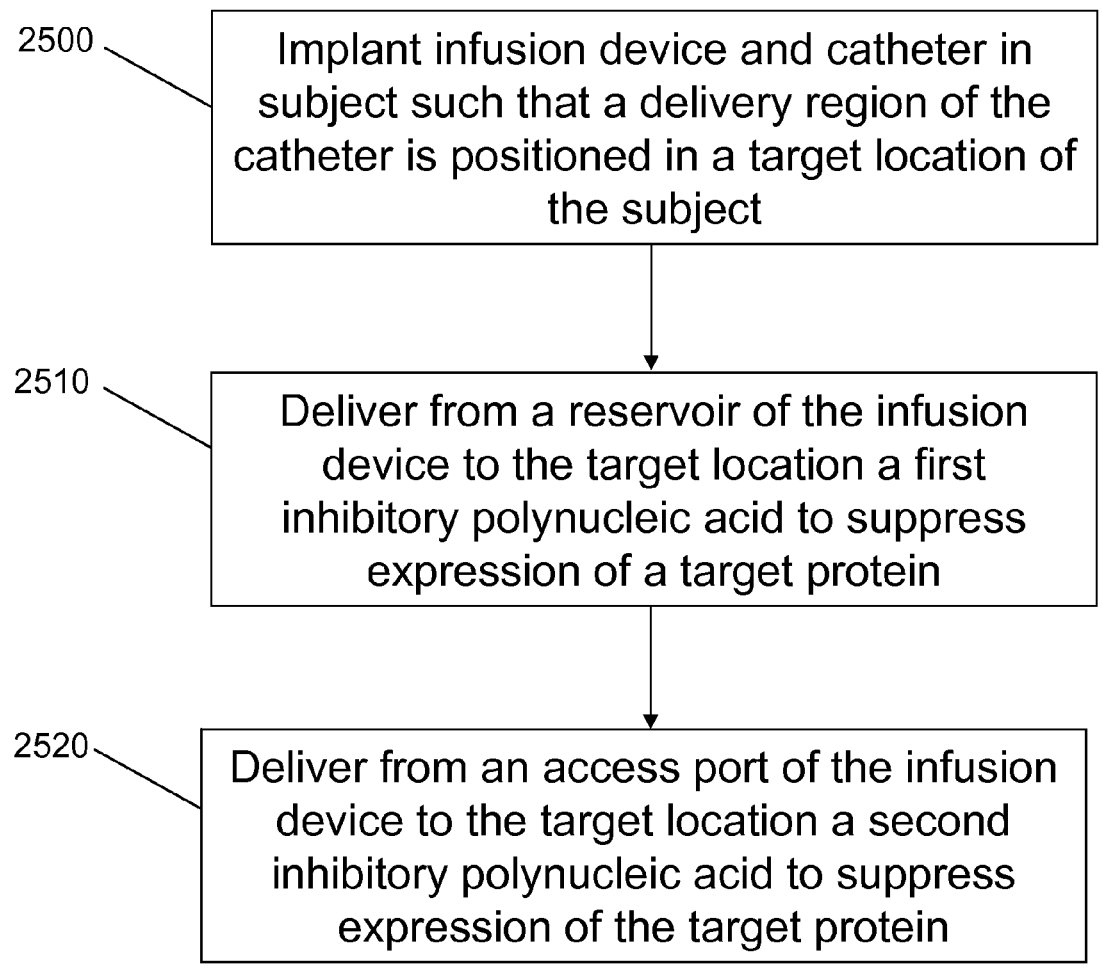

Referring to FIG. 11, another representative method is shown as a flow diagram. The method includes implanting an infusion device 300 and a catheter 100 in a subject such that a delivery region 40 of the catheter is positioned in a target location of a subject (2500). The method further includes delivering from a reservoir 340 of the infusion device 300 to the target location a first composition containing a first inhibitory polynucleic acid configured to suppress expression of a target protein (2510). The method further includes delivering from an access port 320 of the infusion device 300 to the target location a second composition containing a second inhibitory polynucleic acid configured to suppress expression of the target protein (2510). The first inhibitory polynucleic acid preferably is a short acting polynucleic acid, such as an siRNA, and therefore readily reversible. Once it has been established that the patient is tolerating the therapy well (or once an allele-specific therapy becomes available), the access port can be used to deliver a longer acting second inhibitory polynucleic acid, such as an shRNA, which may inhibit expression of the target protein for up to years or more.

Figure 12:
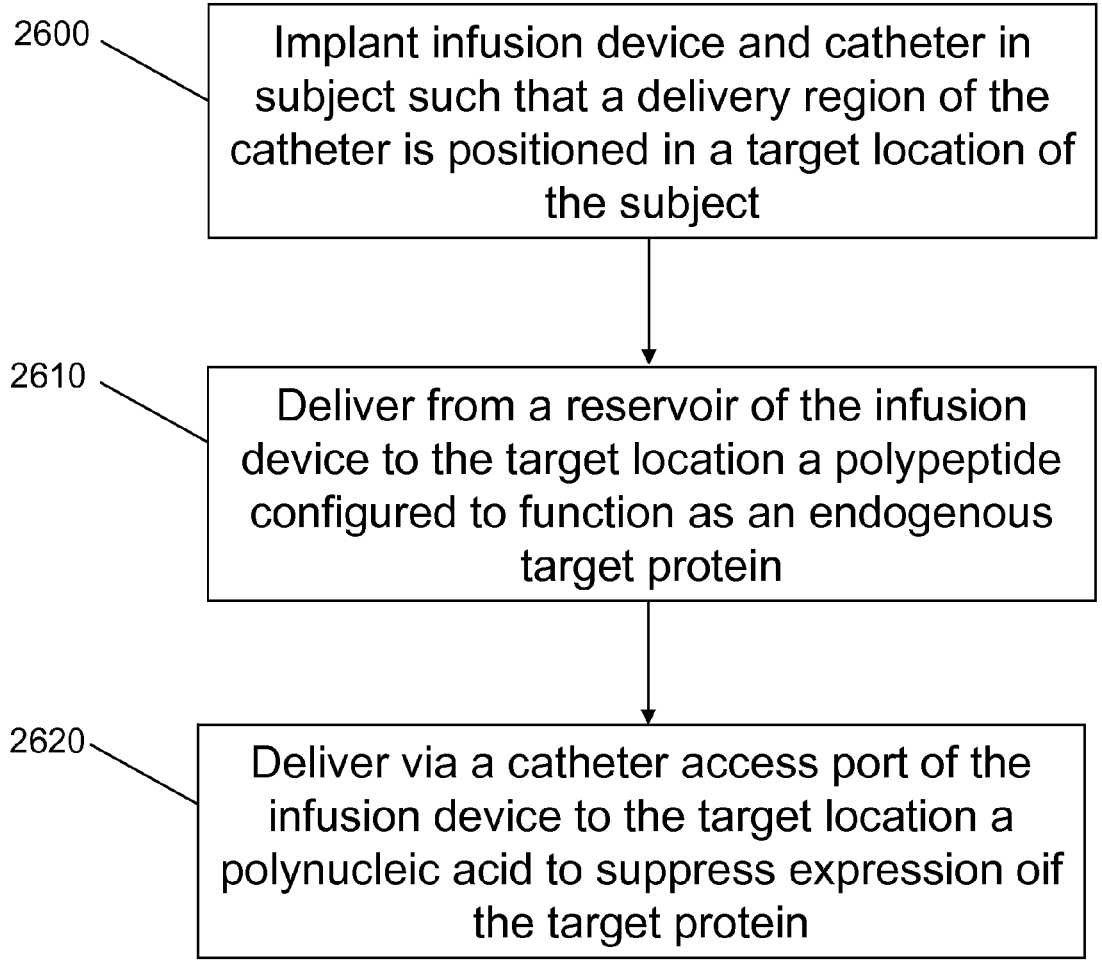

Referring to FIG. 12, another representative method is shown as a flow diagram. The method includes implanting an infusion device 300 and a catheter 100 in a subject such that a delivery region 40 of the catheter is positioned in a target location of a subject (2600). The method further includes delivering from a reservoir 340 of the infusion device 300 to the target location a first composition containing a polypeptide configured to function as an endogenous target protein (2610). The method further includes delivering from an access port 320 of the infusion device 300 to the target location a second composition containing an inhibitory polynucleic acid configured to suppress expression of the target protein (2510). The inhibitory polynucleic acid is preferably a long-acting inhibitory polynucleic acid, such as an shRNA.

It will be understood that the methods depicted in FIGS. 7-12 are merely examples of the many ways in which implantable infusion devices 300 having a reservoir 340 and a catheter access port 320 may be exploited for therapeutic or investigatory advantage. It will be further understood that, while discussed above as a combination of polypeptide and polynucleic acid delivery, the methods described herein may be employed with a combination of polypeptide and small molecule therapy or polynucleic acid and small molecule therapy.

It will be further understood that the methods described herein may be performed in any suitable order and do not necessarily have to conform to the order presented in the flow diagrams depicted herein, and may in some circumstances be performed simultaneously or during overlapping periods of time. It will also be understood that the designations "first" and "second", as they may relate to compositions or agents, is simply for purposes of distinguishing between two agents or compositions (event though in various embodiments they may be the same) and does not imply that the "first" composition or agent is to be administered before the "second" composition or agent. In addition, some steps of the depicted methods may be omitted or additional steps may be added as appropriate. Further, steps from the various different embodiments presented herein may be combined in any suitable manner.

When employing the methods, systems and catheters described above, it may be desirable to deliver therapeutic agents, such as large molecules, in a bolus fashion. Bolus delivery may be achieved in any suitable fashion. For example, bolus delivery may be achieved via injection into an access port or may be achieved through use of a programmable implantable infusion pump, such as Medtronic, Inc.'s SynchroMed® series of pumps. Bolus delivery may impart convection of the therapeutic agent in a subject's CSF and may result in greater distribution of the therapeutic agent in the brain than continuous infusion. However, for chronic delivery or where multiple deliveries over time are desirable, it may be desirable to keep the catheter patent. One way to keep the catheter patent is to infuse a low level of therapeutic agent chronically and infuse boluses on top of the background continuous infusion.

IV. Intrathecal administration to C3 or above

The methods described herein with regard to delivery of therapeutic compositions to a target location of a subject via a reservoir and an access port are applicable regardless of the target location. However, for the sake of clarity and illustration, delivery of therapeutic compositions to the intrathecal space of a subject, particularly to intrathecal space at a level of C3 or higher, e.g. the cisterna magna, will be described in more detail.

As presented herein, it has been found that delivery of therapeutic agent to the intrathecal space at or above the level of C3 of the spinal canal serves to enhance broad delivery of the therapeutic agent to brain tissue. It will be understood that a level of C3 or above includes a level of C2 or above, C1 or above, or in the cisterna magna. Discussed below are a few illustrative methods for delivering a therapeutic agent to the intrathecal space at a level of C3 or higher. While the illustrative methods described below refer to use of catheter 100 and infusion device 300, as described above, it will be understood that any suitable catheter or infusion device may be employed in the described methods.

Figure 13:
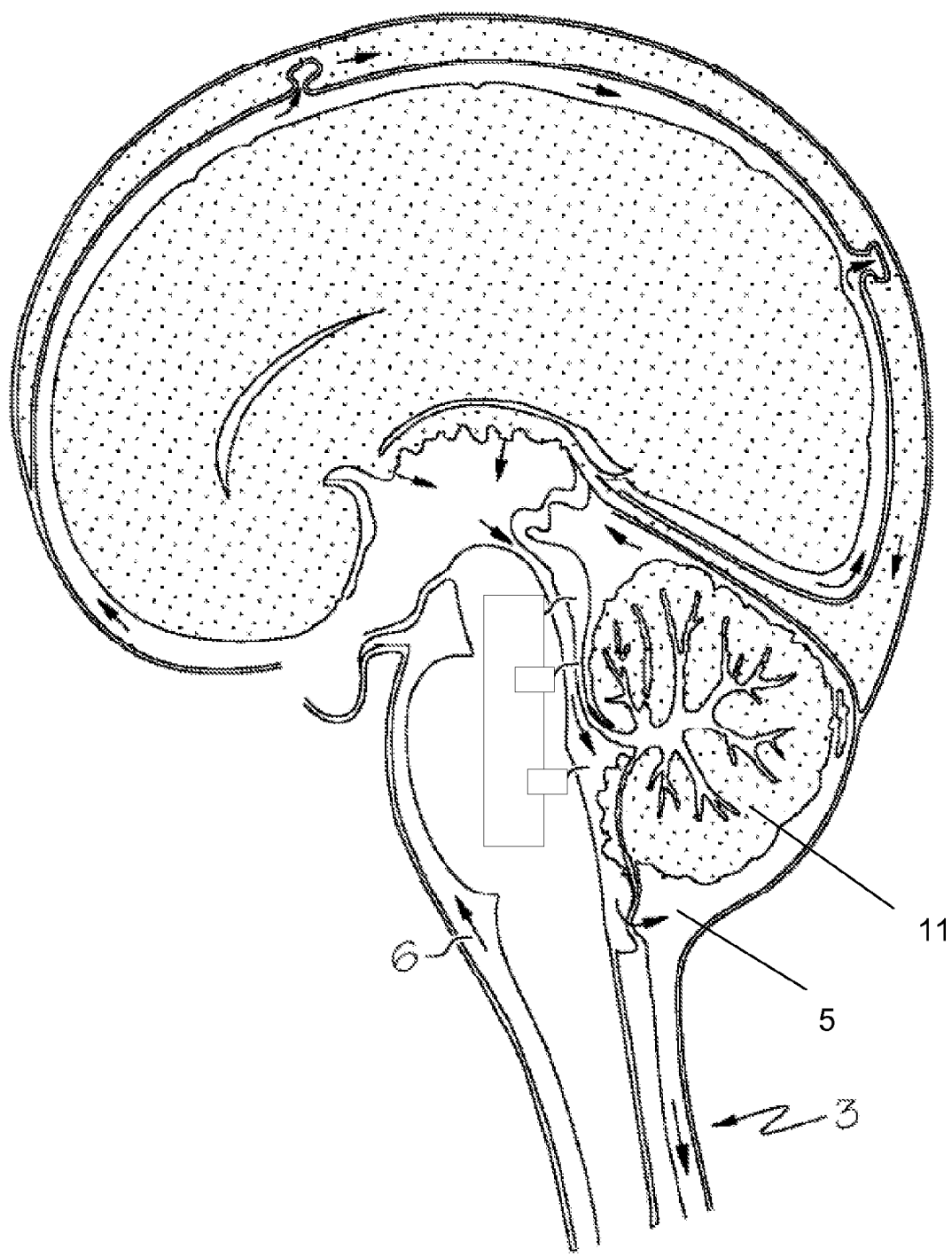
FIG. 13 is a schematic diagram showing typical flow patterns of cerebrospinal fluid through a human central nervous system.

Referring to FIG. 13, a diagrammatic illustration of cerebrospinal fluid (CSF) 6 flow in subarachnoid space 3 of a human is shown. As used herein, "intrathecal" means the delivery of a substance to the subarachnoid space. The subarachnoid space 3 is a compartment within the central nervous system that contains CSF 6. CSF 6 exits the foramen of Magendie and Luschka to flow around the brainstem and cerebellum. The arrows within the subarachnoid space 3 in FIG. 6 indicate CSF 6 flow. CSF 6 is produced in the ventricular system of the brain and communicates freely with the subarachnoid space 3 via the foramina of Magendie and Luschka. The cistema magna 5 is the CSF 6 filled space below the cerebellum 11.

A. Advancement of Catheter Through Spinal Canal

In various embodiments, delivery region 40 of catheter 100 is advanced up the spinal canal to a level of C3 or above. The catheter 100 may be introduced to the intrathecal space of the spinal canal through any known or future developed technique. On example includes introduction through standard lumbar puncture techniques. Once distal portion 20 of catheter 100 gains access to the intrathecal space of the spinal canal, distal end 30 of catheter 100 is advanced rostrally through the spinal canal until a delivery region 40 of catheter 100 is at a level of C3 or above. Distal end 30 of catheter 100 may be advanced rostrally through the use of a stylet.

Catheter 100 may be secured, e.g. by sutures, near the entrance to the intrathecal space. Proximal end 10 of catheter 100 may be tunneled subcutaneously to a region of the body where proximal end 10 may be connected with an infusion device 300.

Regions where chronically implantable infusion devices 300 may be placed, and thus to where proximal end 10 of catheter 100 may be tunneled, include the abdominal region, over the ribs, or in the pectoral region, such as the low pectoral region.

Figure 14:
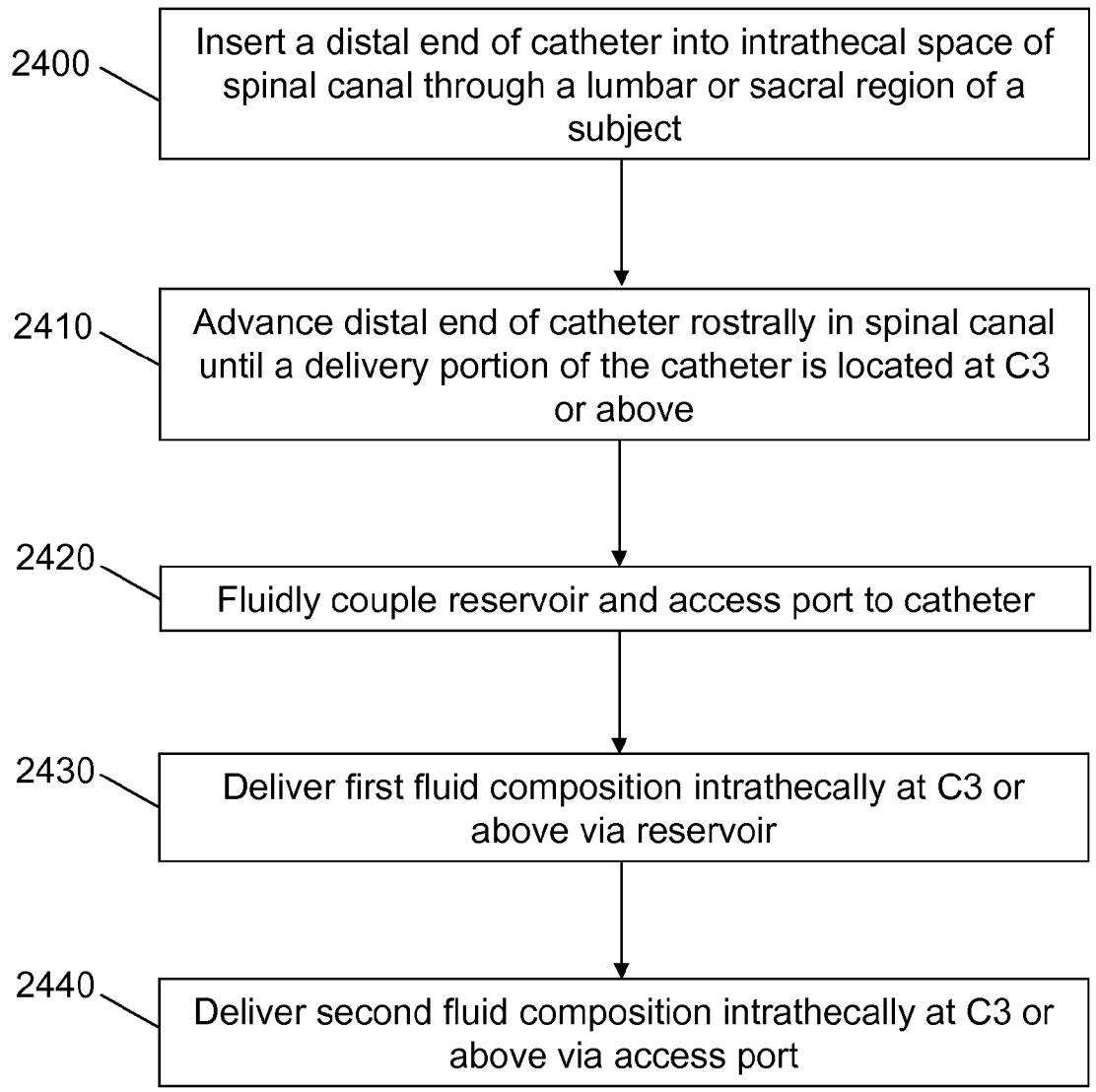
FIG. 14 is a flow diagram illustrating a representative method.

Referring to FIG. 14, an overview of a representative method is illustrated in a flow diagram. The method includes inserting a distal end 30 of a catheter 100 into intrathecal space of a subject's spinal canal through a lumbar or sacral puncture (2400), and advancing the distal end 30 of the catheter 100 rostrally in the spinal canal until a delivery region 40 of the catheter 100 is located at a level of C3 or above (2410). The catheter 100 is fluidly coupled to an access port 320 and a reservoir 340, e.g., by connecting a proximal end 10 of the catheter 100 to a catheter connector 320 of an infusion device 300. A first fluid composition is delivered to the target location, in this case intrathecally at C3 or above, via the reservoir 340. A second fluid composition is delivered to the target location via the access port 320.

B. Cisterna Magna Puncture

In numerous embodiments, a delivery region 40 of catheter 100 is introduced directly into the cisterna magna. This can be accomplished through any known or future developed technique. One suitable technique is to introduce delivery region 40 of catheter 100 through a direct puncture of the cisterna magna. By way of example, standard introducer tool techniques for placement of a catheter into the intrathecal space may be used. If catheter 100 has a visualization marker, surgical navigation instrumentation may be employed to verify that delivery region 40 of catheter 100 is within the cisterna magna. A portion of catheter 100 external to the cisterna magna may be secured, e.g. using sutures, e.g. with a suture sleeve, or using any other know or future developed technique.

From a location outside the cisterna magna, proximal end 10 of catheter 100 may be placed within the subject at a location suitable for connection to an infusion device 300 or may remain outside the body where therapeutic agent may be administered into catheter 100. The location of infusion device 300 will generally depend, among other things, on its size, shape, and conformability. For example, infusion device 300 may be implanted behind the ear, as done with many implantable cochlear devices, or in the pectoral region of the subject. Typically, rigid devices having a volume of 80 cc or less may be comfortably placed in the pectoral region or an adult human. Of course, more flexible material, such as pliable bladders fluidly coupled to an implantable pump, may be comfortably placed in a variety of locations due to the conformability of such bladders. Regardless of where infusion device 300 is located, proximal end 10 of catheter 100 may be tunneled subcutaneously or otherwise to the location of the infusion device 300 and attached thereto.

When infusion device 300 is implanted in a pectoral region or other region of a subject where strain may be placed on catheter 100 due to movement of the subject's head or neck, it may be desirable to place excess catheter 100 proximal to a suture sleeve or anchor external to the cisterna magna to permit strain relief during neck movement. Less excess catheter may be used with implant location behind the ear, as movement of a location behind the ear more closely follows that of the neck.

In various embodiments, an access port is implanted behind a subject's ear and a delivery region 40 of catheter is introduced directly into the subject's cisterna magna.

V. Representative Therapies

The methods and systems described herein may be employed to treat a variety of diseases or may be used in a variety of studies to determine the effects on subjects.

A. Enzyme Replacement Therapy

As discussed above, subjects suffering from or at risk of diseases for which protein replacement could be therapeutic may be benefited by the systems and methods described herein.

One class of proteins for which replacement may be desirable is enzymes. Enzyme replacement therapy to treat CNS disorders typically requires about 10% of the endogenous enzyme to be replaced. Accordingly, in various embodiments, replacement polypeptides or polynucleic acids encoding a second polypeptide capable of producing an enzymatic effect are administered to a subject according to the methods presented herein in an amount sufficient to cause the enzyme or polypeptide to reach a level of about 10% or more of that endogenously present in a normal subject in a location where the enzyme or polypeptide may produce a beneficial effect. A "normal subject", as used herein, means (i) a subject that is free of the CNS enzymatic disorder to be treated or (ii) an average of subjects that are free of the CNS enzymatic disorder. One exemplary enzyme is alpha-L-iduronidase, such as Aldurazyme®, which may be used to treat mucopolysaccharidosis Type I ("MPS-I" or more commonly called Hurler or Hurler-Sheie Syndrome).

Treatment of MPS-I by the methods described herein may be most beneficial if the replacement polypeptide or polynucleic acid encoding the second polypeptide is introduced to the intrathecal space of a subject at a level of C3 or above.

The methods described in FIGS. 7-9 may be useful in subjects suffering from or at risk of diseases associated with a thickening of the meninges, such as MPS-I. For such diseases, delivery of the appropriate polypeptide may result in thinning of the meninges which may assist subsequent polynucleic acid delivery to the brain through the thinned meninges. A determination as to whether the meninges have sufficiently thinned may be made prior to delivery of the polynucleic acid, e.g. by imaging techniques, or the nucleic acid may be administered after sufficient time has passed for the meninges to have thinned. Similarly, it will be understood that any agent capable of enhancing passage of a large molecule to the brain tissue from the CSF may be desirable to administer.

B. Gain of Function Diseases

The methods described herein, particularly as discussed with regard to FIG. 10, may be advantageously applied to treat any disease resulting from a gain of toxic function mutation. Examples of diseases resulting from a gain of toxic function include Huntington's disease, spinocerebellar ataxia type 1, and other diseases characterized by a CAG triplet repeat expansion in the protein-coding region of a gene. By advantageously employing an infusion device 300 having a reservoir 340 and a catheter access port 320, an inhibitory polynucleic acid may be administered to a target location to suppress expression of the mutant gene and a replacement polypeptide may be administered to the target location using the same device 300 to replace the function of the wild-type gene product. For example, it is unclear what long term effects may result from suppressing expression of the huntingtin gene in Huntington's disease patients, particularly if both the wild-type and mutant forms are suppressed. Therefore, the methods described herein may be employed to deliver a polynucleic acid encoding for a replacement polypeptide to subjects receiving inhibitory polynucleic acid therapy. It will be understood that for a variety of the gain of toxic function diseases discussed above, it may be desirable to administer therapeutic agents directly to the parenchyma of the brain rather than administering through the CSF.

VI. Therapeutic Compositions

According to the methods described herein fluid compositions including polypeptides or polynucleic acids may be administered to target locations of subjects. It will be understood that the compositions are fluid at room temperature.

Fluid compositions include solutions, suspensions, dispersions, and the like. Fluid solutions, suspensions, or dispersions may be formulated according to techniques well-known in the art (see, for example, Remington's Pharmaceutical Sciences, Chapter 43, 14th Ed., Mack Publishing Co., Easton, Pa.), using suitable dispersing or wetting and suspending agents, such as sterile oils, including synthetic mono- or diglycerides, and fatty acids, including oleic acid.

Fluid compositions comprising polypeptides and polynucleic acids may be prepared in water, saline, isotonic saline, phosphate-buffered saline, citrate-buffered saline, and the like and may optionally mixed with a nontoxic surfactant. Dispersions may also be prepared in glycerol, liquid polyethylene, glycols, DNA, vegetable oils, triacetin, and the like and mixtures thereof. Under ordinary conditions of storage and use, these preparations may contain a preservative to prevent the growth of microorganisms. Pharmaceutical dosage forms suitable for injection or infusion include sterile, aqueous solutions, suspensions, or dispersions or sterile powders comprising an active ingredient which powders are adapted for the extemporaneous preparation of sterile injectable or infusible solutions or dispersions. Preferably, the ultimate dosage form is a sterile fluid and stable under the conditions of manufacture and storage. A liquid carrier or vehicle of the solution, suspension or dispersion may be a diluent or solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. Proper fluidity of solutions, suspensions or dispersions may be maintained, for example, by the formation of liposomes, by the maintenance of the desired particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin. Excipients that increase solubility, such as cyclodextrin, may be added.

The concentration of polypeptide or polynucleic acid may be readily determined and varied as conditions warrant based on the disease to be treated or the response of the subject to the treatment.

For prolonged delivery of a fluid composition to a subject, it may be desirable for the composition to be isotonic with the tissue into which the composition is being delivered. For example, the fluid composition may be isotonic with a subject's blood or CSF. CSF typically has a tonicity of about 305 mOsm. Accordingly, fluid compositions intended for intrathecal delivery may advantageously have a tonicity of about 290 mOsm to about 320 mOsm. If during formulation the composition has a tonicity lower than about 290 mOsm to about 320 mOsm, the tonicity may be enhanced by adding a tonicity enhancing agent, such as sodium chloride. As used herein, "tonicity enhancing agent" means a compound or composition that increases tonicity of a composition. However, such tonicities of between about 290 mOsm to about 320 mOsm are not always achievable. For example, high concentrations of polypeptides or polynucleic acids themselves when dissolved in water may result in a tonicity of greater than 320 mOsm. When the concentration of polypeptide or polynucleic acid in a fluid composition renders the composition hypertonic relative to a subject's physiological fluid, it is preferred that little or no amount of a tonicity enhancing agent be added to the composition. However, it will be recognized that it may desirable to add one or more additional compounds to the composition even though the addition of the additional compound(s) will further increase tonicity of the composition. For example, it may be desirable to add to the composition an additional therapeutic agent, stabilizing compound, preservative, solubilizing agent, buffer, etc., even though tonicity will be increased.

Sterile fluid compositions may be prepared by incorporating the polypeptide or polynucleic acid in the desired amount in the appropriate diluent or solvent with various other ingredients, e.g. as enumerated above, and, as desired, followed by sterilization. Any means for sterilization may be used. For example, sterilization may be accomplished by heating, filtering, aseptic technique, and the like, or a combination thereof. In some circumstances it may be desirable to obtain a sterile powder for the preparation of sterile injectable solutions. Such sterile powders may be prepared by vacuum drying and freeze-drying techniques, which yield a powder of the active ingredient plus any additional desired ingredient present in a previously sterile-filtered solutions.

Regardless of the large molecule to be delivered, it may be desirable to conjugate the large molecule with a molecule capable of enhancing uptake of the large molecule into cells. Conjugation may be done according to any known or future developed technique with any known or future developed conjugate. One example is the conjugation of polypeptides with mannose, e.g. as described U.S. Patent Publication No. 2005/0208090. U.S. Patent Publication No. 2005/0208090 also describes various other components to compositions that may be useful for delivering molecules to the CNS of a subject, which other components may be useful for the methods and systems discussed herein.

While much of the discussion herein is focused on the delivery of large molecules, it will be understood that the delivery of small molecules (i.e., molecules other than large molecules) to tissues, such as the brain, may also be enhanced by the methods described herein. For example, a first composition containing a drug or small or large molecule and a second composition containing a non-viral or viral vector or a small or large molecule may be delivered to a location within a patient, such as the patient's central nervous system (CNS).

VII. Polypeptides and Polynucleic Acids

Sequences for polypeptides and polynucleic acids suitable for being applied for therapeutic or investigatory purposes as described herein can readily be obtained by those of skill in the art. For example, numerous publications have provided examples of sequences that may be acceptable for protein replacement therapy or for target gene suppression. In addition, the GenBank database or other similar databases may be searched to obtain sequences of proteins or genes of interest. Replacement polypeptides and polynucleic acids encoding replacement polypeptides and inhibitory polynucloetides may readily be designed based on the sequences provided in such databases.

A replacement polypeptide may be synthesized according to known chemical techniques or may be produced and purified via known molecular biological techniques. As such techniques are well known, only a brief overview is provided below.

The form of a polynucleic acid present in a fluid composition as described herein will depend on the intended function of the polynucleic acid. For example, if the polynucleic acid is to serve as gene therapy, the polynucleic acid will be present in an expression vector. Voluminous publications, including published patent applications and patents, describe how to effectively produce expression vectors, and thus are not described herein in detail. In numerous embodiments, the expression vector is a viral expression vector, such as an adeno-associated viral vector.

If the polynucleic acid is an inhibitory polynucleic acid configured to suppress expression of a target gene, the polynucleic acid will be present in a suitable form, such as short interfering nucleic acid (siNA), short interfering RNA (siRNA), double-stranded RNA (dsRNA), micro-RNA (miRNA), short hairpin RNA (shRNA), or the like. A detailed description of suitable forms of such inhibitory polynucleic acids are described in numerous publications, including published patent applications and patents and thus are not described herein in great detail. One example of a patent publication providing a detailed description of inhibitory polynucleotudes is U.S. Patent Application Publication Number 20070270579.

The discussion that follows is similar to that provided in U.S. Published Patent Application No. 20070238642. While the discussion is related to production of a replacement polypeptide, it will be understood that many of the concepts provided below may also be employed with regard to generating a polynucleic acid encoding a second polypeptide for use in the methods described above.

The replacement polypeptide may be made by synthesis in recombinant cell culture. For such synthesis, a polynucleic acid that encodes the replacement polypeptide is secured. DNA encoding the replacement polypeptide molecule may be obtained from tissue in which the endogenous protein is expressed by (a) preparing a cDNA library from these cells, (b) conducting hybridization analysis with labeled DNA encoding the endogenous protein or fragments thereof (up to or more than 100 base pairs in length) to detect clones in the library containing homologous sequences, and (c) analyzing the clones by restriction enzyme analysis or nucleic acid sequencing to identify full-length clones. DNA that is capable of hybridizing to endogenous protein-encoding DNA under low stringency conditions is useful for identifying DNA encoding the endogenous protein. If full-length clones are not present in a cDNA library, then appropriate fragments may be recovered from the various clones using the nucleic acid sequence information and ligated at restriction sites common to the clones to assemble a full-length clone encoding the endogenous protein or replacement polypeptide. Alternatively, genomic libraries will provide the desired DNA.

Once this DNA has been identified and isolated from the library it may be ligated into a replicable vector for further cloning or for expression. For example, a peptide-encoding gene can be expressed in mammalian cells by transformation of the mammalian cells with an expression vector comprising DNA encoding the peptide. It is preferable to transform host cells capable of accomplishing such peptide expression so as to obtain the peptide in the culture medium or periplasm of the host cell, e.g., obtain a secreted molecule.

The vectors and methods for obtaining a replacement polypeptide disclosed herein may be suitable for use in host cells over a wide range of prokaryotic and eukaryotic organisms. In general, of course, prokaryotes are preferred for the initial cloning of DNA sequences and construction of vectors. For example, E. coli K12 strain MM 294 (ATCC No. 31,446) is particularly useful. Other microbial strains that may be used include E. coli strains such as E. coli B and E. coli X1776 (ATCC No. 31,537). These examples are, of course, intended to be illustrative rather than limiting.

Prokaryotes may also be used for expression. The aforementioned strains, as well as E. coli strains W3110 (F-, lambda-, prototrophic, ATCC No. 27,325), K5772 (ATCC No. 53,635), and SR101, bacilli such as Bacillus subtilis, and other enterobacteriaceae such as Salmonella typhimurium or Serratia marcesans, and various pseudomonas species, may be used.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, E. coli is typically transformed using pBR322, a plasmid derived from an E. coli species (see, e.g., Bolivar et al., Gene, 2: 95 [1977]). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the b-lactamase (penicillinase) and lactose promoter systems (Chang et al., Nature, 375: 615 [1978]; Itakura et al., Science, 198: 1056 [1977]; Goeddel et al., Nature 281: 544 [1979]) and a tryptophan (trp) promoter system (Goeddel et al., Nucleic Acids Res., 8: 4057 [1980]; EPO Appl. Publ. No. 0036,776). While these are commonly used, other microbial promoters have been discovered and utilized, and details concerning their nucleotide sequences have been published, enabling a skilled worker to ligate them functionally with plasmid vectors (see, e.g., Siebenlist et al., Cell, 20: 269 [1980]).

In addition to prokaryotes, eukaryotic microbes, such as yeast cultures, may also be used. Saccharomyces cerevisiae, or common baker's yeast, is the most commonly used among eukaryotic microorganisms, although a number of other strains are commonly available. For expression in Saccharomyces, the plasmid YRp7, for example (Stinchcomb et al., Nature, 282: 39 [1979]; Kingsman et al., Gene, 7: 141 [1979]; Tschemper et al., Gene, 10: 157 [1980]), is commonly used. This plasmid already contains the trp1 gene that provides a selection marker for a mutant strain of yeast lacking the ability to grow in tryptophan, for example, ATCC No. 44,076 or PEP4-1 (Jones, Genetics, 85: 12 [1977]). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., J. Biol. Chem., 255: 2073 [1980]) or other glycolytic enzymes (Hess et al., J. Adv. Enzyme Reg., 7: 149 [1968]; Holland et al., Biochemistry, 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure [Tissue Culture, Academic Press, Kruse and Patterson, editors (1973)]. Examples of such useful host cell lines are VERO and HeLa cells, Chinese hamster ovary (CHO) cell lines, and W138, BHK, COS-7, 293, and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication [Fiers et al., Nature, 273: 113 (1978)]. Smaller or larger SV40 fragments may also be used, provided there is included the approximately 250-bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Satisfactory amounts of protein are produced by cell cultures; however, refinements, using a secondary coding sequence, serve to enhance production levels even further. One secondary coding sequence comprises dihydrofolate reductase (DHFR) that is affected by an externally controlled parameter, such as methotrexate (MTX), thus permitting control of expression by control of the methotrexate concentration.

In selecting a preferred host cell for transfection by the vectors of the invention that comprise DNA sequences encoding both replacement polypeptide and DHFR protein, it is appropriate to select the host according to the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the Chinese hamster ovary (CHO) cell line deficient in DHFR activity, prepared and propagated as described by Urlaub and Chasin, Proc. Natl. Acad. Sci. (USA) 77: 4216 (1980).

On the other hand, if DHFR protein with low binding affinity for MTX is used as the controlling sequence, it is not necessary to use DHFR-deficient cells. Because the mutant DHFR is resistant to methotrexate, MTX-containing media can be used as a means of selection provided that the host cells are themselves methotrexate sensitive. Most eukaryotic cells that are capable of absorbing MTX appear to be methotrexate sensitive. One such useful cell line is a CHO line, CHO-K1 (ATCC No. CCL 61).

Construction of suitable vectors containing the desired coding and control sequences employs standard ligation techniques. Isolated plasmids or DNA fragments are cleaved, tailored, and religated in the form desired to prepare the plasmids required. If blunt ends are required, the preparation may be treated for 15 minutes at 15° C. with 10 units of Polymerase I (Klenow), phenol-chloroform extracted, and ethanol precipitated.

Size separation of the cleaved fragments may be performed using 6 percent polyacrylamide gel described by Goeddel et al., Nucleic Acids Res., 8: 4057 (1980).

For analysis to confirm correct sequences in plasmids constructed, the ligation mixtures are typically used to transform E. coli K12 strain 294 (ATCC 31,446) or other suitable E. coli strains, and successful transformants selected by ampicillin or tetracycline resistance where appropriate. Plasmids from the transformants are prepared and analyzed by restriction mapping and/or DNA sequencing by the method of Messing et al., Nucleic Acids Res., 9: 309 (1981) or by the method of Maxam et al., Methods of Enzymology, 65: 499 (1980).

After introduction of the DNA into the mammalian cell host and selection in medium for stable transfectants, amplification of DHFR-protein-coding sequences is effected by growing host cell cultures in the presence of approximately 20,000-500,000 nM concentrations of methotrexate, a competitive inhibitor of DHFR activity. The effective range of concentration is highly dependent, of course, upon the nature of the DHFR gene and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

Of course, it will be understood that the above discussion only provides an illustration of some of the ways in which microbiological or recombinant techniques may be applied to generate polypeptides and poly nucleic acids useful with the methods described herein. It will be further understood that any suitable method for preparing such large molecules may be employed.

EXAMPLE

I. Overview

A total of fifteen canines were implanted in this study to get 12 animals to term. Canines were randomly placed into four groups: (1) Bolus, (2) Buffer only Control Group, (3) Low dose chronic Aldurazyme group, (4) High dose chronic Aldurazyme group. Bolus animals received four weekly injections of Aldurazyme into the cisterna magna. These animals were euthanized two days post final bolus injection. All remaining groups had an intrathecal catheter surgically implanted into the sub-arachnoid space surrounding the spinal cord with the distal outlet of the catheter externalized and connected to an external pump that was placed in the pocket of the jacket worn by the animal. Pumps were programmed to deliver infusate (designated treatment) at a rate of 56 microliters per hour. The externalized pumps had small reservoirs that were removed and replaced with freshly filled reservoirs containing the designated treatment once every other day. At the end of 21 days the pumps were turned off. At 23 days the animals were euthanized.

Pumps were refilled every 2 days with 3 ml of infusate (buffer, low dose Aldurazyme, or high dose Aldurazyme). During the refill procedure the residual volumes of fluid in the reservoir were weighed and the volume was measured. The programmed flow rate of the pump implies that a total of approximately 2.69 ml should have been delivered. This volume of course is contingent on the time of day that actual change outs occurred. The residual volume amounts measured are acceptable and the data supports that the catheters were continuously patent for the duration of the study and that appropriate volume of infusate was delivered.

Fluoroscopic images indicated that for all animals that had catheters implanted that the catheters' tip location was not significantly changed throughout the study duration.

Histopathologic analysis revealed a difference in response to the various treatment groups. Treatment groups could be ranked from those causing the least tissue change to those causing the most tissue changes: Catheter with buffer, Aldurazyme bolus, low-dose Aldurazyme thru catheter, and high dose Aldurazyme thru catheter.

For all animals, canine brain and spinal cord tissue samples were prepared and blind coded. Alpha-L-iduronidase levels in the tissues were determined on via biochemical assay. The alpha-L-iduronadase data supports that there were statistically significant differences among experimental groups in terms of Aldurazyme uptake in the tissue.

In this study, chronic, continuous delivery of Aldurazyme enzyme into the cerebrospinal fluid (CSF) of normal dogs via the intrathecal route resulted in detectable elevation of alpha-L-iduronidase enzyme levels in various regions of the brain and spinal cord tissue above endogenous levels. Pump residual volume data supports that the catheter was patent throughout the study and that infusate was delivered. The fluoro images of the implanted system showed no evidence of movement documenting stability and integrity of the implanted hardware and noting delivery as close to C1 as possible. Histopathologic results note a difference in tissue response to the various treatment groups. The alpha-L-iduronadase data supports that there were statistically significant differences among experimental groups in terms of Aldurazyme uptake in the tissue. The data from this preclinical study demonstrates there are differences in terms of Aldurazyme penetration levels with regard to the different modes of dosing.

II. Study Design

Dogs were randomly placed into four groups, with three dogs per group: (1) Bolus Aldurazyme control group: These dogs received four weekly injections of Aldurazyme into the CSF of the cisterna magna, at a dose of 1 milligram per injection. The standard Aldurazyme formulation (0.58 mg/ml of recombinant human alpha-L-iduronidase, 150 mM NaCl, 100 mM sodium phosphate, pH 5.8, and 0.001% polysorbate 80) as manufactured by Genzyme, was used. This group replicated the treatment studied by Kakkis et al. (2004). All remaining animals had an intrathecal catheter surgically implanted into subdural space surrounding the spinal cord, with the distal outlet of the catheter positioned in the high thoracic region. The body of the catheter was anchored securely and passed transcutaneously to the external pump and placed in the pocket of the jacket worn by the dog. (2) Buffer only control group: The pump reservoir in these dogs was filled with the standard formulation buffer only (150 mM NaCl, 100 mM sodium phosphate, pH 5.8, 0.001% polysorbate 80, as supplied by Genzyme) with no enzyme. The pump was programmed to deliver 56 microliters of solution to the intrathecal CSF per hour. This group controlled for any possible unforeseen effects of the chronic delivery of the formulation buffer. (3) Low dose chronic Aldurazyme group: The pump reservoir was filled with Aldurazyme diluted 1:4 with the standard formulation buffer to an enzyme concentration of 0.145 mg/ml. The pump was programmed to deliver 56 microliters per hour of solution to the intrathecal CSF, delivering a cumulative total of 4.0 mg of Aldurazyme over 21 days. This group of dogs received the same cumulative amount of Aldurazyme over the same cumulative number of days as the bolus Aldurazyme control group. (4) High dose chronic Aldurazyme group: the pump reservoir was filled with Aldurazyme in the standard formulation buffer at a concentration of 0.58 mg/ml. The pump was programmed to deliver 56 microliters per hour of solution to the intrathecal CSF, delivering a cumulative total of 16.0 mg of Aldurazyme over 21 days. This group of dogs received four times the cumulative amount of Aldurazyme, over the same cumulative number of days, as the other treated groups. The pumps selected for this study had small reservoirs that were removed and replaced with reservoirs containing fresh solution (Low dose Aldurazyme, High Dose Aldurazyme, or buffer only) once every other day. At the end of 21 days the pumps reservoirs were emptied and the pumps were turned off. At day 23 post-op the animals were euthanized.

III. Acronyms

In this Example section, "CSF" refers to cerebrospinal fluid, "CBC" refers to complete blood count, and "IDU" refers to iduronadase. "Aldurazyme" refers to alpha-L-iduronidase available from Genzyme Therapeutics, 500 Kendall Street, Cambridge, Mass. 02142. Aldurazyme is a registered trademark of BioMarin/Genzyme LLC. "Paradigm" pump refers to an external infusion device available from Medtroinc MiniMed, Inc. 18000 Devonshire Street, Northridge, Calif. 91325-1219. Paradigm is a registered trademark of Medtronic MiniMed Inc.

IV. Test Articles, Control Articles and Test Systems

A Medtronic Minimed Paradigm 508 pump was used to deliver compositions to the test subjects as follows: Low Dose Continuous Aldurazyme; Low dose continuous intrathecal infusion of Aldurazyme (0.145 mg/ml, cumulative dose of 4.0 mg over 21 days); and High Dose Continuous Aldurazyme; High dose continuous intrathecal infusion of Aldurazyme (0.58 mg/ml, cumulative dose of 16.0 mg over 21 days) via Paradigm 508 pump.

Aldurazyme (BioMarin Pharmaceutical Inc. 105 Digital Drive, Novato, Calif. 94949) was supplied as a sterile solution in clear glass 5 mL vials (2.9 mg idronidase per 5 mL), and was stored under refrigeration at 2 C to 8 C (36 to 46 F). (The instructions "DO NOT FREEZE OR SHAKE" were followed). The diluted solution was used immediately.

A Paradigm 508 pump was used to deliver continuous intrathecal infusion of the formulation buffer for Aldurazyme, but enzyme-free. Aldurazyme was delivered in four weekly bolus injections of 1 mg of Aldurazyme into the cisterna magna (replicates condition from a previously published study, Kakkis et al., 2004, *Molecular Genetics and Metabolism*).

Intrathecal catheters were fabricated from PE-10 tubing having an o.d. of 0.61 mm and an i.d. of 0.28 mm. A platinum radiopaque marker band near the delivery region of the catheter was used to verify navigation and placement of the catheter.

The subjects used in this study were adult male dogs weighing from 23-24 kg obtained from a USDA Class A breeder.

V. Pre-Implant

Pre-operative antibiotics were started prior to surgery, and pre-operative analgesics were started within 24 hrs of surgical procedure. Animals were induced with a short acting barbiturate or short acting hypnotic. Isoflurane was used to maintain the animal at an appropriate plane of anesthesia. Comparable substitutes were used on occasion by veterinary discretion. Steroid medications were not given.

The animals were fasted prior to surgery and were bathed within 48 hrs of surgical procedure.

Complete blood count (CBC) including white blood cell differentiation, red blood cell morphology, and coagulation testing was done within ten days prior to the day of implant.

VI. Surgery

Animals were kept on rotating antibiotics for the duration of the study. With the exception of D#328904 that was termed at 24 days due to a holiday, all animals were termed 23 days after implant.

TABLE 1

Implant Scheme: duration and infusate

| Dog Number | Implant Date or First Treatment Date | Euthanasia Date | Duration of Implant or of Treatment | Infusate |
| --- | --- | --- | --- | --- |
| 001491 | May 3, 2005 | May 26, 2005 | 23 days | Bolus |
| 328904 | May 9, 2005 | Jun. 2, 2005 | 24 days | Bolus |
| 328899 | May 16, 2005 | Jun. 8, 2005 | 23 days | Buffer |
| 328907 | May 17, 2005 | Jun. 9, 2005 | 23 days | Buffer |
| 328976 | May 31, 2005 | Jun. 23, 2005 | 23 days | Low dose |
| 328968 | Jun. 6, 2005 | Jun. 29, 2005 | 23 days | High dose |
| 328901 | Jun. 7, 2005 | Jun. 30, 2005 | 23 days | Bolus |
| 328971 | Jun. 29, 2005 | Jul. 22, 2005 | 23 days | High dose |
| 328978 | Jun. 29, 2005 | Jul. 22, 2005 | 23 days | High dose |
| 329018 | Jul. 11, 2005 | Aug. 3, 2005 | 23 days | Low dose |
| 329020 | Jul. 11, 2005 | Aug. 3, 2005 | 23 days | Low dose |
| 329017 | Jul. 13, 2005 | Aug. 5, 2005 | 23 days | Buffer |

For dogs receiving pumps with intrathecal catheters, a hemi-laminectomy was performed. The catheter was implanted into the intrathecal space via lumbar puncture, and the delivery region was advanced rostrally and positioned as close to the cisterna magna as possible. A stylet was inserted into the lumen to assist in advancement of the catheter. The proximal catheter segment was anchored. Catheter was tunneled to subcutaneous pocket on animal's right side, distal portion was externalized and connected to Paradigm 508 pump. The drug pump was filled with appropriate solution (depending upon experimental group to which animal had been assigned), and programmed to deliver 56 ul/hr. The pump was then placed into pocket of the jacket on the animal's right side. All incisions were closed.

For dogs receiving bolus injections of Aldurazyme, a needle was placed into the cisterna magna and one milligram of Aldurazyme (1.72 ml) was delivered slowly as a bolus injection into the cisterna magna. Needle placement was confirmed by return of CSF. Needle was removed and puncture wound was dressed as needed.

The final location of catheter placement was documented via lateral and dorsoventral fluoro images.

VII. Termination

The dogs were euthanized two days following the final delivery of Aldurazyme bolus or pump infusion (23 days post-surgery). Briefly, sedatives were given to the animals. The animals were induced with a short acting barbiturate or short acting hypnotic. Isoflurane was used to maintain the animals at an appropriate plane of anesthesia. CSF and CBC samples, as well as final fluoroscopic images (for canines with catheters) were collected prior to termination. Brain and spinal cord tissue samples were harvested and fixed in 10% neutral buffered formalin (NBF).

The time from euthanasia to freezing of the brain tissue samples ranged from approximately 13 to 22 minutes (average 16 minutes) and did not differ across the treatment groups. The time from euthanasia to freezing of the spinal cord tissue samples ranged from approximately 26 to 46 total minutes (average 34 minutes, includes the time to harvest the brain tissue samples) and also did not differ across the treatment groups.

All the canine CNS tissue samples used for the enzyme assay were stored at −80° C. from the time of harvest until dissection. At the time of dissection, six samples were removed from the −80° C. freezer at a time and maintained on dry ice. For each sample, one at a time, the tissue was allowed to thaw at room temperature only to the point necessary to enable cutting of the tissue. The tissue was dissected to produce a "superficial" and "deep" tissue sample of approximately 150-250 milligrams net weight, and each superficial or deep sample was placed into its own individually prenumbered 1.5 mL cryovial. The tubes and tissue were then immediately returned to dry ice, and thence to −80 ° C. long-term storage until shipment for biochemical analysis.

Each sample (dog and brain or cord region) was prepared using its own bench-top cutting surface and disposable scalpel (or Teflon tube, for cord samples, see below) to prevent cross-contamination of samples. Similarly, the experimenter changed gloves between the processing of each anatomical region and experimental group (high, low, bolus, control) to prevent inadvertent carry-over of enzyme from group to group or anatomical region within group.

All samples were blind coded for analysis.

Spinal cords samples were dissected to obtain "superficial" and "deep" tissue samples such that the deep tissue samples were free of any spinal meninges. To achieve this, a piece of teflon tubing, approximately 0.125 inches (3 mm) outer diameter was used to obtain a "core" piece of central spinal cord (predominantly gray matter) by inserting the teflon tubing longitudinally into the partially thawed spinal cord section. The resulting inner core sample was then removed from within the teflon tubing as the deep tissue sample, while the remaining outer tissue (consisting predominantly of meningeal tissue and spinal white matter tracts) was designated the superficial tissue sample.

In two instances, because of the small diameter of the cord in these individual dogs, the volume of tissue was insufficient to collect both a deep and superficial tissue sample. In dog #329017 (buffer only group, lumbar cord) insufficient tissue mass remained associated with the outer meninges following removal of the "core" deep sample to have sufficient mass for the enzyme assay. Thus, the "superficial lumbar" sample is missing for this dog. In dog #328968 (high dose pump group, thoracic cord) the sample was too small to attempt dissection, so the entire sample was considered a "superficial" tissue sample, and the corresponding "deep" tissue sample was treated as missing data.

For each of the sampled brain regions, the tissue was harvested at time of necropsy as an approximately 1 cm thick coronal "slab" of tissue. To prepare a deep and superficial tissue sample from each slab, the tissue was laid flat on a fresh cutting surface and thawed at room temperature just enough to enable a wedge of tissue to be cut from the tissue. The wedge of tissue was then dissected with a transverse cut positioned a minimum of 3 millimeters inward from the pial surface of the wedge. Care was taken to err, if necessary, on the deeper side (i.e., positioning the cut more than 3 millimeters from the pial surface, e.g. 4 or 5 millimeters inward). The resulting segment of tissue including the pial surface was designated the superficial sample, while the inward portion of the wedge of tissue was designated the deep sample.

A necessary consequence of this dissection procedure in the brain is that the superficial samples are predominantly gray matter (cerebellar molecular layer or cerebral cortical layers) and the deep samples may contain substantially more white matter (cerebellar granular layer and axonal tracts, or cerebral coronal radiata, etc.) Nevertheless, the procedure permits the assessment of whether the exogenously applied enzyme was able to penetrate the CNS tissue by a substantial distance.

Tissues were prepared for α-L iduronidase assay as follows. Tissues were trimmed to 100-200 mg and minced in a plastic petri dish with a fresh, sharp razor blade. The minced tissue was transferred to a fresh an unused homogenizer on ice, three volumes (vol:wt) of cold PAD buffer +0.1% triton was added, but not less than 150 μl. Keeping the tissue grinder within ice all the time, the tissue was homogenized thoroughly, using a minimum of 30 strokes. The homogenates were transferred to microcentrifuge tubes and immediately placed on ice. Samples and controls were incubated as follows: three replicates of tissue sample (25 μl sample+25 μl 6 mM 4-MUI substrate); three substrate blanks (25 μl PAD+triton+25 μl 6 mM 4-MUI substrate); and two tissue blanks (25 μl sample+25 μl 0.4M formate buffer, pH 3.5).

The α-L iduronidase assay was performed generally as set forth in the following table:

| Canine tissue | μl used in assay | Dilution | Incubation time (minutes) |
| --- | --- | --- | --- |
| Brain | 25 | (1:50) 10 μl homogenate + 490 μl PAD | 30 |
| Spinal Cord & meninges | 25 | (1:50) 10 μl homogenate + 490 μl PAD | 30 |
| CSF | 25 | none | 30 |

The reaction was stopped with 1 ml of glycine-carbonate buffer. A blank was prepared using 1 ml glycine carbonate. A standard was prepared after completely thawing in a 37 degree centigrade water bath and vortexed vigorously before pipetting. To 20 μl of the 4-MU standard, 2 ml glycine carbonate was added. The samples were centrifuged for 1 min at 6,000 rpm to pellet any cellular debris.

The 4-MU standard was prepared as follows: 20 μl 4-MU standard was pipetted into 2 mL glycine carbonate. After using glycine carbonate to zero the machine, a Perkin-Elmer fluorometer was calibrated so that 1 nanomole equals 2,000 fluorescence units, by setting the auto conc. to 1000.

A cuvette was thoroughly rinsed and absorbance was read at 365 excitation/440 emission.

Enzyme activity was calculated according to the following equation (A unit of iduronidase is defined as nanomoles of 4-MUI substrate cleaved per hour):

$$\frac{net\ F.U.s}{time} \times \frac{60\ min}{1\ hour} \times \frac{1\ nmol\ 4\text{-}MU}{2000\ F.U.s} \times \frac{1}{0.025\ mL} \times dilution\ factor = units/ml\ iduronidase$$

On the same day, a BioRad protein determination was determined (linear range of the assay is 1.5-10 µg/ml). The dye will had a bluish tinge the high end of the range was approached. The protein determination was performed by diluting homogenate 1:40 by adding 10 µl to 390 µl pyrogen-free $H_2O$. Ten microliters of the diluted sample was added to 790 µl $H_2O$ for the assay (For CSF assay 10 µl straight to 790 µl $H_2O$). A protein was caluculated according to the following formula:

$$Average\ OD_{595} = \frac{\mu g\ protein\ in\ cuvette}{\mu l\ sample\ in\ cuvette}$$

$$= \mu g\ protein/\mu l\ sample \times dil.\ factor(20)$$

$$= \mu g\ protein/\mu l\ homogenate$$

$$= mg\ protein\ /ml\ homogenate$$

Iduronidase activity was expressed according to the following equation.

$$\frac{units\ iduronidase/ml}{mg\ protein/ml} = units\ of\ iduronidase\ per\ mg\ of\ protein$$

VIII. Statistic Methods

The effects of bolus injections or chronic, continuous delivery of Aldurazyme on level of enzyme activity in the canine CNS tissue samples were analyzed using analysis of variance (ANOVA) to compare enzyme levels across experimental groups for each anatomical region and depth of tissue sample (deep or superficial). For those anatomical regions and tissue depths for which the null hypothesis of no differences among groups was rejected, further comparisons were performed determine which groups differed, using the LSD ("least significant difference") method for pairwise comparisons among groups. All analyses were performed using MedStat for Excel version 5.2.

The enzyme assay data are not normally distributed with similar variances across the experimental groups. Rather, data are positively skewed. That is, many of the data values are clustered at the lower end of the scale, while other values are distributed along a wide range of higher values, stretching out the right hand tail of the distribution.

As a consequence of the skew in the distribution of the enzyme assay data, the assumption of homogeneity of variance across the experimental groups upon which the ANOVA and pairwise comparisons between groups rely is not met. An accepted and recommended method for "normalizing" data distributions that have positive skewness is to perform a logarithmic transformation of the raw data prior to analysis (e.g., see Winer, B. J., *Statistical Principles in Experimental Design*, $2^{nd}$ *Edition*, 1971, p. 400). The log transformed data yielded substantially reduced skewness and more homogenous standard deviations across the experimental groups than do the raw data, enabling for valid tests of group differences by the LSD method. Therefore, all tests of the statistical significance of differences among groups that are reported here were computed using log transformed enzyme assay data. For intelligibility, however, group means are reported as the average of the original, untransformed enzyme assay values.

IX. Results and Discussion

The table below summarizes all of the Analyses of Variance (ANOVAs) testing the null hypotheses of no differences among any of the experimental groups' mean enzyme assay value, by anatomical region and depth of tissue sample. Tests for which the p value is less than 0.05 are shown in boldface.

Summary of ANOVA results by tissue sample depth and anatomical site

| Tissue sample depth | Anatomical site | Mean square Treatment Effect | Mean square Error | F ratio (df = 3, 8) | P value |
|---|---|---|---|---|---|
| Superficial | Frontal cortex | 0.214 | 0.172 | 1.243 | 0.3565 |
| Superficial | Diencephalon/parietal cortex | 0.256 | 0.008 | 30.686 | 0.0001 |
| Superficial | Occipital cortex | 0.471 | 0.005 | 89.329 | 0.0000 |
| Superficial | Cerebellum | 0.789 | 0.063 | 12.520 | 0.0022 |
| Superficial | Thoracic cord | 1.218 | 0.233 | 5.226 | 0.0004 |
| Superficial | Lumbar cord | 0.610 | 0.172 | 3.542 | 0.0678 |
| Deep | Frontal cortex | 0.009 | 0.009 | 1.049 | 0.4225 |
| Deep | Diencephalon/parietal cortex | 0.049 | 0.005 | 10.743 | 0.0035 |
| Deep | Occipital cortex | 0.027 | 0.034 | 0.803 | 0.5264 |
| Deep | Cerebellum | 0.304 | 0.069 | 4.397 | 0.0417 |
| Deep | Thoracic cord | 0.332 | 0.048 | 6.959 | 0.0128 |
| Deep | Lumbar cord | 0.257 | 0.020 | 13.104 | 0.0019 |

There were statistically significant differences among the experimental groups in terms of Aldurazyme enzyme uptake into the superficial tissue layers in all anatomical regions tested except for those most remote from the site of enzyme delivery, i.e., the frontal cortex and the lumbar spinal cord. The average enzyme assay values for the superficial tissue samples for each treatment group, by anatomical region, are shown in the table below.

| Enzyme assay values in superficial tissue samples, by region (mean ± s.d. idu/mg protein) | | | | | | |
|---|---|---|---|---|---|---|
| Treatment group | Frontal cortex | Diencephalon/ parietal cortex | Occipital cortex | Cerebellum | Thoracic cord | Lumbar cord |
| Bolus injections | 68.2 ± 31.1 | 58.2* ± 21.1 | 100.8* ± 25.3 | 312.7* ± 126.0 | 418.3* ± 14.6 | 435.8 ± 553.2 |
| High dose pump | 97.5 ± 142.5 | 15.1 ± 1.8 | 16.7 ± 1.4 | 98.2* ± 65.0 | 635.1 ± 1011.6 | 64.9 ± 44.7 |
| Low dose pump | 25.2 ± 20.7 | 13.9 ± 1.5 | 17.4 ± 2.9 | 68.9* ± 21.1 | 48.6* ± 23.3 | 31.4 ± 19.8 |
| Buffer only | 17.7 ± 6.8 | 14.9 ± 2.1 | 14.3 ± 1.1 | 16.7 ± 3.9 | 14.6 ± 3.5 | 27.6 ± 25.7 |

*p < 0.05 vs. buffer only control group.

No differences in the enzyme activity level in superficial lumbar cord tissue were observed among the treatment groups at traditional significance levels ($p=0.0678$). However, because it would be paradoxical to see elevations of enzyme activity in deep lumbar cord tissue without also seeing some elevation in the superficial tissue, additional pairwise comparisons were performed to help fully understand the data.

The null hypothesis of no difference in enzyme levels across treatment groups in superficial thoracic cord was rejected with a high degree of confidence ($p=0.00036$). However, high variability in the assay values across dogs in the high dose pump group (mean=635.1 with standard deviation ±1011.6) resulted in unequal variances across groups making meaningful pairwise difficult. However, omitting the high dose pump group from the analysis indicates that there were statistically significant differences among the bolus, low dose pump, and buffer only groups by ANOVA ($p=0.01767$). Post-hoc t-tests indicate that enzyme activity levels in superficial tissue from the thoracic cord are significantly elevated over the buffer only control group in both the group receiving weekly bolus injections ($p=0.00007$, one-tailed), and the group receiving the low dose, continuous delivery of Aldurazyme ($p=0.00868$, one-tailed).

There were statistically significant differences among the four treatment groups in enzyme levels in the superficial tissue of the cerebellum (ANOVA $p=0.00217$). Pairwise comparisons among groups indicate that all groups receiving Aldurazyme, whether by bolus injection, high dose continuous pumping, or low dose continuous pumping, had elevated enzyme levels relative to the buffer only control group ($p<0.05$ in all cases). Furthermore, the enzyme levels attained in this tissue by the dogs receiving the weekly bolus injections was significantly higher than that attained by either high dose or low dose continuous administration ($p<0.05$). The difference between the two pump groups (high versus low dose pump) was not statistically significant.

Although the elevation of enzyme activity in the superficial tissue of the occipital cortex resulting from bolus injections of Aldurazyme was, on average, only about one-third as great as in the superficial tissue of the cerebellum, the elevation was highly statistically significant ($p<0.00001$), and was 7-fold greater than the buffer only group. No elevation of enzyme levels in this tissue over the levels obtained in dogs in the buffer only group was observed in the dogs in either the high or low dose pump conditions. Similarly, the difference between levels attained by dogs in the high dose versus low dose pump group was not statistically significant.

As with the superficial tissue samples from the occipital cortex, the samples from the parietal cortex showed significant elevation in enzyme levels in the dogs receiving the weekly bolus injections over the enzyme levels of each of the other groups ($p<0.05$). No elevation of enzyme levels in this tissue over levels obtained in dogs in the buffer only group was observed in the dogs in either the high or low dose pump conditions. The difference between levels attained by dogs in the high dose versus low dose pump group was not statistically significant.

No statistically significant difference in enzyme levels among the four treatment groups was observed in the superficial tissue samples from the frontal cortex.

Although the magnitude of the differences were not as pronounced as for the superficial tissue samples, there were statistically significant differences among the experimental groups in terms of Aldurazyme uptake in the deep tissue samples in most of the anatomical regions tested. Specifically, there were differences among treatment groups in Aldurazyme uptake into deep tissue samples in the diencephalon/ parietal cortex, cerebellum, thoracic cord, and lumbar cord. The average enzyme assay values for the deep tissue samples for each treatment group, by anatomical region, are shown in the table that follows.

| Enzyme assay values in deep tissue samples, by region (mean ± s.d. idu/mg protein) | | | | | | |
|---|---|---|---|---|---|---|
| Treatment group | Frontal cortex | Diencephalon/ parietal cortex | Occipital cortex | Cerebellum | Thoracic cord | Lumbar cord |
| Bolus injections | 18.4 ± 4.2 | 26.0* ± 5.2 | 34.1 ± 9.0 | 89.8* ± 21.7 | 5.94* ± 43.0 | 38.1* ± 20.9 |

-continued

| Enzyme assay values in deep tissue samples, by region (mean ± s.d. idu/mg protein) | | | | | | |
|---|---|---|---|---|---|---|
| Treatment group | Frontal cortex | Diencephalon/ parietal cortex | Occipital cortex | Cerebellum | Thoracic cord | Lumbar cord |
| High dose pump | 16.6 ± 4.1 | 18.8 ± 2.7 | 32.3 ± 12.9 | 72.4* ± 40.9 | 50.0* ± 36.5 | 35.4* ± 8.9 |
| Low dose pump | 14.0 ± 1.5 | 13.1 ± 1.4 | 25.6 ± 11.1 | 54.2 ± 48.1 | 14.7 ± 2.7 | 11.4 ± 1.3 |
| Buffer only | 14.3 ± 3.3 | 15.2 ± 2.4 | 22.6 ± 11.6 | 16.7 ± 4.7 | 12.2 ± 5.1 | 10.5 ± 2.9 |

*p < 0.05 vs. buffer only control group

The ANOVA test for differences among the four treatment groups in enzyme activity levels in deep samples of lumbar cord was significant at $p<0.002$. The pairwise comparisons among the groups by the LSD method indicated that the enzyme level in the bolus injection group was significantly higher than the buffer only control group and the low dose pump group ($p<0.05$). Likewise, the enzyme level in the high dose pump group was significantly higher than the buffer only control group and the low dose pump group ($p<0.05$). There was no significant difference between the bolus injection and high dose pump group, which were each elevated an average of about 3-fold over the enzyme level of the buffer only control group (see above).

As noted earlier, it would be paradoxical to see significant elevation of enzyme levels in the deep tissue samples from the lumbar cord without also seeing elevation in the superficial tissues. The analysis of the superficial lumbar tissues was hindered somewhat by missing data from dog #329017 (buffer only group), for which insufficient tissue mass remained associated with the outer meninges following removal of the "core" deep sample to have sufficient mass for the enzyme assay of a "superficial" sample. The average enzyme assay value of the other two dogs in this control group was substituted for the "missing" value of this third dog to enable some additional analyses to further understand the data. Following this substitution, a t-test of the difference between the bolus injection group and the control group is significant ($p=0.0383$, one-tailed), as is a t-test of the difference between the bolus injection group and the low dose pump group ($p=0.04269$, one-tailed), although the difference between the high dose pump group and the control group does not attain significance. While these analyses might be suspect in isolation, the results indicate that the observation of significant elevation of enzyme levels in the deep lumbar tissue samples in the bolus injection and high dose pump groups is not contradictory and paradoxical vis-a-vis the enzyme assay values in the superficial tissue.

A deep tissue sample for dog #328968 (high dose pump group, thoracic cord) was not available. To enable ANOVA and LSD computations by MedStat 5.2, the average of the other two dogs in the high dose pump group was used as a proxy for this missing value.

The resulting ANOVA indicated that there are statistically significant differences among the four groups ($p=0.01279$), and the pairwise comparisons showed that both the bolus injection group and the high dose pump group had significantly elevated enzyme assay values in the deep thoracic cord tissue compared to the buffer only control group and the low dose pump group ($p<0.05$). The enzyme assay values in the bolus injection and high dose pump groups were each approximately 4-fold greater than the values in the other groups. There was no significant difference between the low dose pump group and the control group, and no significant difference between the bolus injection group and the high dose pump group.

The ANOVA test for differences among the four treatment groups in enzyme activity levels in deep samples of cerebellum was significant ($p=0.04171$). The pairwise analysis of deep tissue samples from the cerebellum revealed significant elevation of the enzyme assay levels in the bolus injection group and high dose pump groups over the buffer only control group ($p<0.05$). No other pairwise comparisons were significant.

No significant differences among the four treatment groups were obtained with regards to the enzyme levels in the deep tissue samples of the occipital cortex.

Despite the lack of differences among the groups in the deep tissue samples of the occipital cortex, a statistically significant difference among groups was observed in the deep tissue samples from the diencephalon/parietal cortex region ($p=0.00353$). Pairwise comparisons showed that the bolus injection group values were significantly elevated vis-á-vis the buffer only control group and each of the other two groups ($p<0.05$). Paradoxically, the pairwise comparisons also showed the high dose pump group values to be greater than the low dose pump group values ($p<0.05$) even though neither the low nor high dose pump groups were significantly elevated in comparison to the buffer only control group. Perhaps this significance test constitutes a Type I error (i.e., false rejection of the null hypothesis, for which there is a 5% chance), in part due to the fact that the average assay value for the low dose pump group was actually (and non-significantly) even lower than the control groups' average.

No significant differences among the four treatment groups were obtained with regards to the enzyme levels in the deep tissue samples of the frontal cortex.

Consistent with previous studies [Kakkis et al., *Mol Genet Metab*. 2004 September-October; 83(1-2):163-74], the current study showed that four weekly bolus injections of 1.0 mg (in 1.7 mL) recombinant alpha-L-iduronidase into the cisterna magna of the normal canine results in statistically significant elevations in enzyme activity levels in many regions of the brain and spinal cord. The elevation can be substantial, attaining enzyme levels that are 28-fold over control levels in superficial tissues of the thoracic cord. Elevation in deeper regions of tissue are less extreme but still substantial, attaining enzyme levels of 5.4-fold, 4.9-fold and 3.6-fold over control levels in the cerebellum, thoracic cord, and lumbar cord, respectively.

The primary objective of this study was to determine whether chronic, continuous delivery of Aldurazyme into the CSF of a normal dog via an intrathecal route can also result in detectable elevation of the enzyme activity level above endogenous levels, in various regions of the brain and spinal cord. The data obtained show that chronic, continuous delivery of Aldurazyme into the canine CSF does result in detectable elevation of enzyme levels in superficial regions of the thoracic cord and cerebellum, and, with a higher dose, in deeper regions of the cerebellum, and thoracic and lumbar cord.

The second objective of this study was to compare two different dosage levels of continuous Aldurazyme delivery with each other, and with intermittent bolus delivery.

The data show a dosage difference between the two chronic, continuous delivery conditions. The higher dosage resulted in detectable elevation of enzyme activity levels more broadly (in more regions of the CNS) than the lower dosage. Also, in the thoracic and lumbar cord, the higher dosage resulted in a higher elevation of enzyme activity than was obtained with the lower dosage.

However, the data also show that intermittent bolus delivery of Aldurazyme into the cisterna magna was superior to chronic, continuous delivery of Aldurazyme into the high cervical intrathecal space, both in terms of distribution of enzyme (reflected by elevation of enzyme levels more remote from the delivery site) and amount of enzyme elevation attained in superficial and deeper CNS tissues. In fact, there was no region of the CNS tissue in which chronic, continuous delivery of Aldurazyme resulted in better results (higher enzyme activity) than intermittent bolus delivery even with a chronic, cumulative dose that was four times greater than the cumulative dose delivered by the bolus injections.

Figure 15:
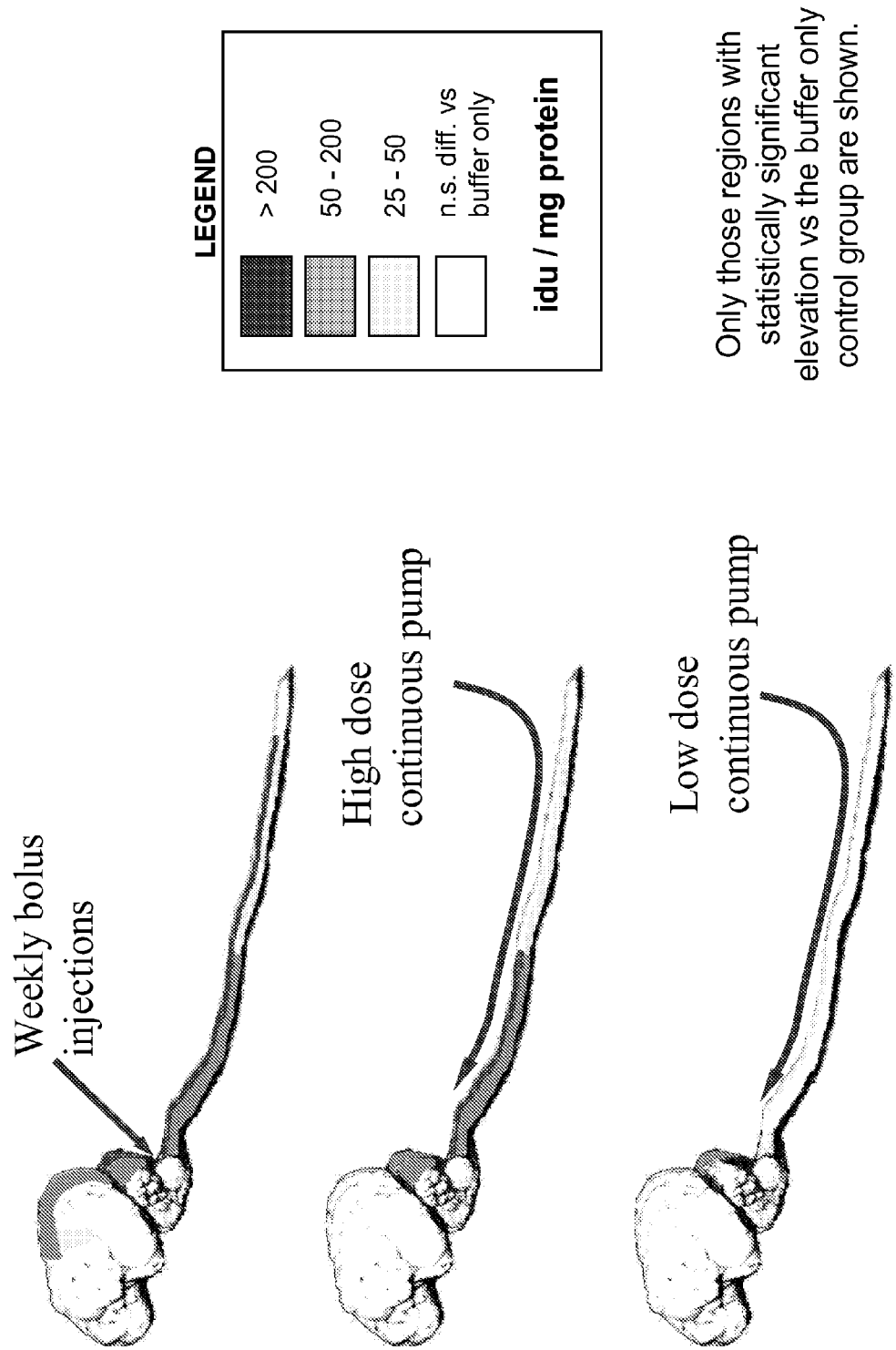
FIG. 15 is a schematic depiction of the distribution of Aldurazyme® in the CNS of dogs in a study performed as discussed with regard to the Example presented herein.

FIG. 15 provides a visual summary of the results of this study in terms of distribution and "uptake" of the exogenously administered enzyme.

It is not possible to definitively know from the data of this study how much of the Aldurazyme in the tissue resided in the interstitial fluid, and how much was taken up into the cells of the CNS in a manner that would result in increased catalysis of glycosaminoglycans in the lysosomes. However, 48 hours elapsed between the last delivery of Aldurazyme and the termination of the dogs in this study, which exceeds the estimated half-life of turn-over of interstitial fluid in the brain of many mammalian species (e.g., 6-16 hours in rat and rabbit, [Abbot, 2004]) by a factor of at least three. Therefore, it is likely that most of the enzyme activity detected in the tissue samples was due to Aldurazyme that was intracellular. It has been shown by fluorescence microscopy [Belichenko et al, Penetration, diffusion, and uptake of recombinant human alpha-L-iduronidase after intraventricular injection into the rat brain. *Mol Genet Metab*. 2005 September-October; 86(1-2): 141-9] that intracerebroventricular administration of exogenous recombinant human alpha-L-iduronidase in the rat brain results in uptake of the enzyme into vesicular structures within neurons (probably lysosomes). Furthermore, since alpha-L-iduronidase is known to produce effective intracellular enzyme activity in non-CNS tissues when delivered systemically, and in CNS cells when taken up from paracrine sources [Desmaris et al, Prevention of neuropathology in the mouse model of Hurler syndrome. *Ann Neurol*. 2004 July; 56(1):68-76], there is reason to expect that Aldurazyme delivered to the CNS tissues by either the bolus injections or chronic, continuous infusion would be not only intracellular but also metabolically active in the cells of the CNS.

It is not possible to definitively know from the data of this study whether the bolus injections into the cisterna magna resulted in greater elevation of enzyme levels in some deep tissue samples of the brain only because of greater "penetration" of the enzyme into the tissue (e.g., movement into the tissue from the CSF down a concentration gradient) or also because of better distribution of a "sufficient concentration" of enzyme via the CSF into the ventricular system. Significantly elevated enzyme was obtained in deep tissue samples of the diencephalon/parietal lobe but not the deep tissue samples of the occipital lobe. This is consistent with the possibility that the elevation of enzyme in the diencephalon was due more to the movement of a sufficiently high concentration of enzyme (delivered by bolus injection into the cistern magna) into the lateral ventricles, rather than to penetration of enzyme from the dorsal surface of the brain.

In either case, however, the data lead to the conclusion that intermittent bolus delivery of Aldurazyme or other large molecules is likely to be superior in terms of clinical benefit to the patient compared to chronic, continuous delivery into the intrathecal space, even with a four-fold higher cumulative dose. Therefore, if an implantable drug pump is to be used as a means of delivering the large molecule, it would be advantageous for the drug pump to be programmable, allowing for boluses of the enzyme to be delivered according to a periodic schedule. The current data also suggest that it may be desirable for the site of the bolus delivery (position of the distal tip of the delivery catheter) to be as close to the cisterna magna as possible, rather than more caudal in the intrathecal space of the spinal cord.

It is likely that the buoyancy (relative baricity) of the Aldurazyme formulation in CSF will be a consideration with regards to the optimal delivery site in (usually vertical) humans compared to the (usually horizontal) canine posture. In addition, delivery into the cerebral ventricles of patients should be considered, since even in the canine brain (substantially smaller than the human brain) elevation of enzyme in the frontal lobe was not found using the cisterna magna as the delivery site. Further pre-clinical studies will be needed to determine the optimal delivery site for enzyme replacement therapy to the cerebrum.

X. Conclusions

Chronic, continuous delivery of Aldurazyme into the canine CSF results in detectable elevation of enzyme levels in superficial regions of the thoracic cord and cerebellum, and, with a higher dose, in deeper regions of the cerebellum, and thoracic and lumbar cord.

Intermittent bolus delivery of Aldurazyme into the cisterna magna is superior to chronic, continuous delivery of Aldurazyme into the high cervical intrathecal space, both in terms of distribution of enzyme and amount of enzyme elevation attained in superficial and deeper CNS tissues. Increasing the cumulative dose of chronically delivered Aldurazyme by as much as a factor of four does not alter this conclusion.

Treatment of the neurological pathology in MPS I patients by direct delivery of Aldurazyme into the CSF compartment using a chronically implantable pump may be feasible, assuming no barriers arise due to safety issues (potential immune response in patients) or issues of compatibility and stability of Aldurazyme with the delivery device.

An implantable drug pump used for this purpose should be programmable, allowing for boluses of the enzyme to be delivered according to a periodic schedule. Subject to further pre-clinical studies, the optimal site for delivery of the enzyme is likely to be as far rostral as possible; delivery into the cerebral ventricles should be considered.

Thus, embodiments of METHODS FOR INFUSING FLUIDS VIA AN IMPLANTABLE INFUSION SYSTEM are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for infusing first and second fluid compositions to a target location of a subject using an implantable infusion system including an infusion device and a catheter, the infusion device having a reservoir and a catheter access port, the catheter having a delivery region and being operably couplable to the infusion device such that fluid stored in the reservoir or infused into the access port is deliverable via the delivery region to a target location of the subject, the method comprising:

introducing the delivery region of the catheter into the intrathecal space of the subject at a lumbar level of the spinal canal and advancing the delivery region rostrally in the intrathecal space of the spinal canal to a level of C3 or higher;

introducing into the reservoir the first fluid composition comprising a first polypeptide configured to function as an endogenous protein;

delivering the first fluid composition to the target location via the delivery region of the catheter at a substantially constant low infusion rate sufficient to maintain catheter patency, with intermittent boluses at a higher rate; and delivering to the target location the second fluid composition, wherein the second fluid composition comprises a polynucleic acid encoding a second polypeptide configured to function as the endogenous protein and wherein the second fluid composition is infused into the catheter access port, wherein the first and second polypeptides are the same or different.

2. The method of claim 1, wherein the endogenous protein is an enzyme.

3. The method of claim 1, wherein advancing the delivery region rostrally in the intrathecal space of the spinal canal to a level of C3 or higher comprises advancing the delivery region to the subject's cisterna magna.

4. The method of claim 1, further comprising:

determining whether a condition or symptom of the subject improves prior to delivering the second fluid composition.

* * * * *